(12) United States Patent
Ma et al.

(10) Patent No.: US 11,850,557 B2
(45) Date of Patent: Dec. 26, 2023

(54) INTRINSICALLY MICROPOROUS LADDER-TYPE TRÖGER'S BASE POLYMERS

(71) Applicants: King Abdullah University of Science and Technology, Thuwal (SA); THE BOARD OF TRUSTEES OF THE LELAND STANFORD JUNIOR UNIVERSITY, Stanford, CA (US)

(72) Inventors: Xiaohua Ma, Thuwal (SA); Ingo Pinnau, Thuwal (SA); Holden W. H. Lai, Stanford, CA (US); Yan Xia, Stanford, MN (US)

(73) Assignees: King Abdullah University of Science and Technology, Thuwal (SA); The Board of Trustees of the Leland Stanford Junior University, Stanford, CA (US)

( * ) Notice: Subject to any disclaimer, the term of this patent is extended or adjusted under 35 U.S.C. 154(b) by 470 days.

(21) Appl. No.: 17/273,950

(22) PCT Filed: Sep. 17, 2019

(86) PCT No.: PCT/IB2019/057824
§ 371 (c)(1),
(2) Date: Mar. 5, 2021

(87) PCT Pub. No.: WO2020/058850
PCT Pub. Date: Mar. 26, 2020

(65) Prior Publication Data
US 2022/0023804 A1 Jan. 27, 2022

Related U.S. Application Data

(60) Provisional application No. 62/892,056, filed on Aug. 27, 2019, provisional application No. 62/732,371, filed on Sep. 17, 2018.

(51) Int. Cl.
*B01D 71/62* (2006.01)
*B01D 53/22* (2006.01)
(Continued)

(52) U.S. Cl.
CPC ........... *B01D 71/62* (2013.01); *B01D 53/228* (2013.01); *B01D 69/02* (2013.01); *B01D 71/44* (2013.01);
(Continued)

(58) Field of Classification Search
CPC ...... B01D 71/62; B01D 53/228; B01D 69/02; B01D 71/44; B01D 71/64; B01D 71/76;
(Continued)

(56) References Cited

U.S. PATENT DOCUMENTS 8,575,414 B2 * 11/2013 Liu ......................... C10L 3/101
585/818
11,318,455 B2 * 5/2022 Helms .................. H01M 4/382
(Continued)

FOREIGN PATENT DOCUMENTS

CN        111533731 A   *   8/2020
CN        113549008 A   *   10/2021
(Continued)

OTHER PUBLICATIONS

Notification of Transmittal of the International Search Report and the Written Opinion of the International Searching Authority, or the Declaration for PCT/IB2019/057824 dated Nov. 19, 2019.

*Primary Examiner* — Stephen Hobson
(74) *Attorney, Agent, or Firm* — Billion & Armitage

(57) ABSTRACT

Embodiments of the present disclosure feature an intrinsically microporous ladder-type Tröger's base polymer including a repeat unit based on a combination of W-shaped CANAL-type and V-shaped Tröger's base building blocks, methods of making the intrinsically microporous ladder-
(Continued)

type Tröger's base polymer, and methods of using the intrinsically microporous ladder-type Tröger's base polymer to separate a chemical species from a fluid composition including a mixture of chemical species. Embodiments of the present disclosure further include ladder-type diamine monomers for reacting to form a Tröger's base in situ, and methods of making the ladder-type diamine monomers using catalytic arene-norbornene annulation.

20 Claims, 12 Drawing Sheets

(51) Int. Cl.
  *B01D 69/02*     (2006.01)
  *B01D 71/44*     (2006.01)
  *C08G 73/02*     (2006.01)
  *B01D 71/64*     (2006.01)
  *B01D 71/76*     (2006.01)
  *C07C 209/36*    (2006.01)
  *C07C 211/61*    (2006.01)
  *C08G 73/10*     (2006.01)

(52) U.S. Cl.
  CPC .......... *C08G 73/0273* (2013.01); *B01D 71/64* (2013.01); *B01D 71/76* (2013.01); *B01D 2325/028* (2013.01); *B01D 2325/04* (2013.01); *B01D 2325/22* (2013.01); *B01D 2325/24* (2013.01); *C07C 209/365* (2013.01); *C07C 211/61* (2013.01); *C08G 73/1053* (2013.01); *C08G 73/1064* (2013.01); *C08G 73/1082* (2013.01)

(58) Field of Classification Search
  CPC .......... B01D 2325/028; B01D 2325/04; B01D 2325/22; B01D 2325/24; B01D 2256/24; B01D 2256/245; B01D 2257/102; B01D 2257/104; B01D 2257/108; B01D 2257/11; B01D 2257/504; B01D 2258/0283; B01D 2323/36; B01D 2325/02; C08G 73/0273; C08G 73/1053; C08G 73/1064; C08G 73/1082; C07C 209/365; C07C 211/61; Y02C 20/40; Y02P 20/151

See application file for complete search history.

(56) References Cited

U.S. PATENT DOCUMENTS

| | | | | |
|---|---|---|---|---|
| 11,472,915 | B2 * | 10/2022 | Swager | B01D 53/228 |
| 11,717,803 | B2 * | 8/2023 | Cooper | B01J 20/28069 |
| | | | | 423/245.1 |
| 2013/0267616 | A1 * | 10/2013 | McKeown | C08G 12/26 |
| | | | | 528/401 |
| 2016/0102177 | A1 * | 4/2016 | Ghanem | C08G 73/1078 |
| | | | | 95/55 |
| 2018/0319937 | A1 * | 11/2018 | Hefner, Jr. | B01D 69/02 |
| 2019/0185481 | A1 * | 6/2019 | Ma | C07D 487/08 |
| 2019/0194393 | A1 * | 6/2019 | Ghanem | C08G 73/1082 |
| 2020/0165189 | A1 * | 5/2020 | Abdulhamid | B01D 71/64 |
| 2020/0199141 | A1 * | 6/2020 | Ma | C08G 73/1053 |
| 2021/0013536 | A1 * | 1/2021 | Golden | H01M 8/0228 |
| 2021/0269598 | A1 * | 9/2021 | Pinnau | C07D 487/08 |
| 2022/0411574 | A1 * | 12/2022 | Lai | C09D 165/00 |
| 2023/0160082 | A1 * | 5/2023 | Shirataki | C25B 9/23 |
| | | | | 204/252 |

FOREIGN PATENT DOCUMENTS

| | | | | |
|---|---|---|---|---|
| WO | WO-2017091357 A1 * | 6/2017 | | B01D 53/228 |
| WO | 2017212382 A1 | 12/2017 | | |
| WO | 2018048515 A1 | 3/2018 | | |
| WO | 2018057119 A1 | 3/2018 | | |
| WO | WO-2018048515 A1 * | 3/2018 | | B01D 71/62 |
| WO | WO-2018057119 A1 * | 3/2018 | | B01D 69/02 |
| WO | WO-2018187025 A1 * | 10/2018 | | B01D 67/0006 |
| WO | WO-2019012347 A1 * | 1/2019 | | B01D 53/228 |
| WO | WO-2019012349 A1 * | 1/2019 | | B01D 53/228 |
| WO | WO-2020058850 A1 * | 3/2020 | | B01D 53/228 |
| WO | WO-2022043981 A1 * | 3/2022 | | B01D 53/228 |

* cited by examiner

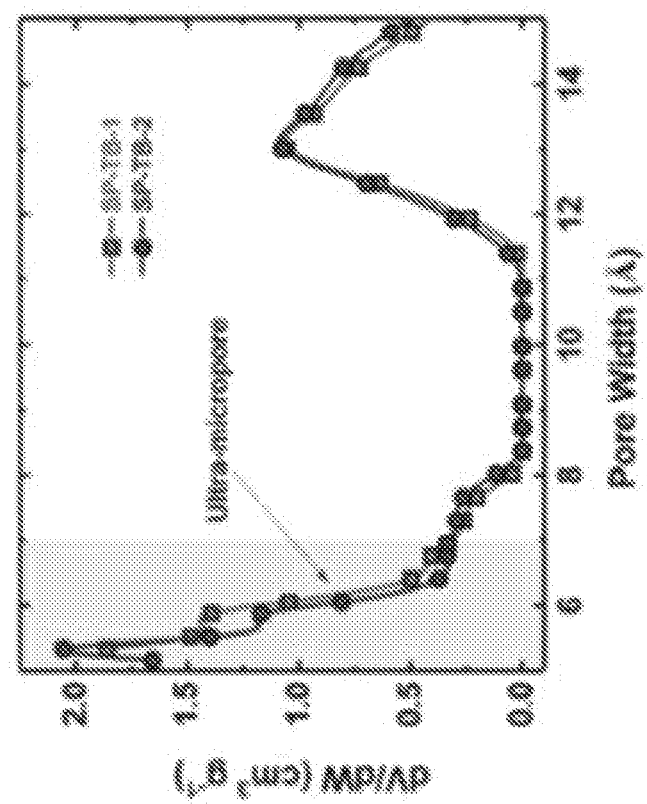
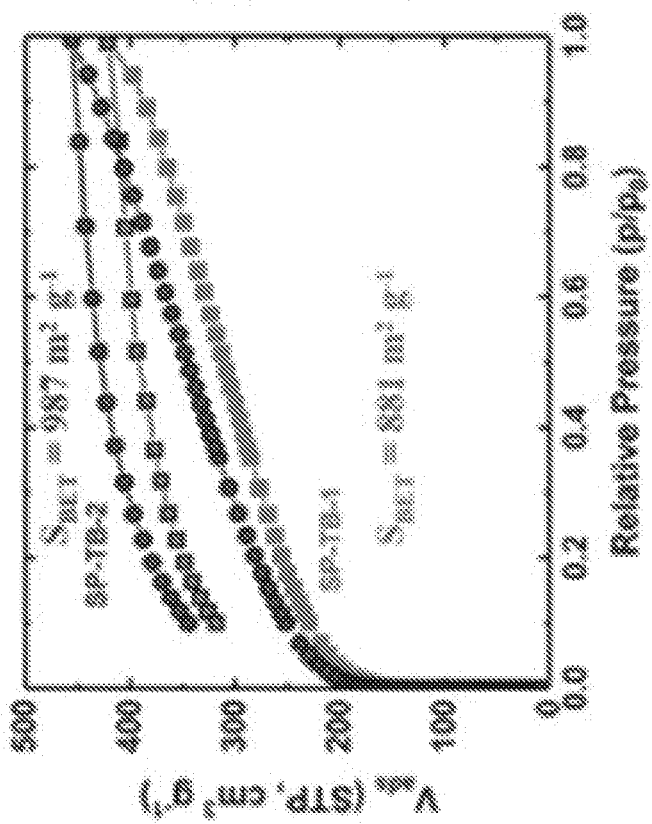
FIG. 9A
FIG. 9B

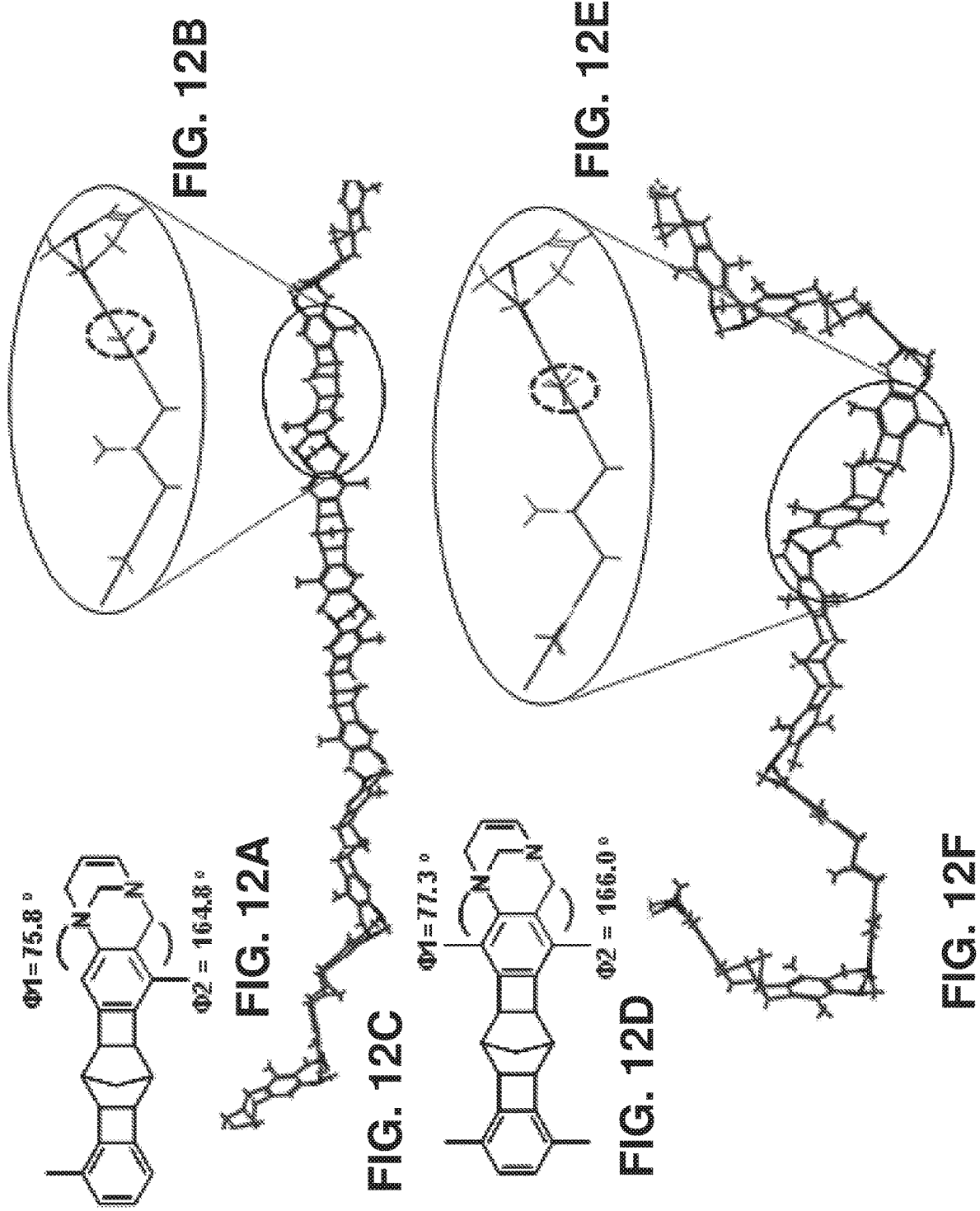

INTRINSICALLY MICROPOROUS LADDER-TYPE TRÖGER'S BASE POLYMERS

BACKGROUND

Membrane-based gas separation processes are emerging in a variety of large-scale industrial applications, such as hydrogen recovery from petrochemical process streams, onsite nitrogen generation ($O_2/N_2$), acid gas removal from natural gas ($CO_2$, $H_2S$), and others. To achieve technically and economically viable processes ideal membranes require high permeability and selectivity. One polymer class that has shown potential as advanced gas separation membrane material is based on polymers of intrinsic microporosity (PIMs). Solution-processible PIMs are an emerging high-performance materials class that has attracted great attention in a variety of fields such as membrane-based gas separation and storage, liquid separation and filtration, catalysis, pervaporation, and sensors. PIMs are extremely rigid, solution processible polymers with large Brunauer-Emmett-Teller (BET) surface area, high gas permeability, and excellent thermal stability. To date, synthesis of ladder-type PIMs is limited by the availability of only a few building blocks with sterically hindered contortion sites. These ladder polymers contain certain types of sterically hindered contortion centers, such as spirobisindane, spirobifluorene, ethanoanthracene, triptycene and Tröger's base.

The key strategy to design PIMs is to incorporate rigid and contorted building blocks in the polymer backbone to frustrate efficient polymer chain packing. This concept has been successfully applied to microporous ladder polymers and intrinsically microporous polyimides (PIM-PIs). Most of the soluble ladder-type PIMs have been synthesized by polycondensation of 2,3,5,6-tetrafluorobenzyl-1,4-dicyanate with "kinked" biscatecols containing core motifs such as tetraphenylethylene-, spirobisindane-, ethanoanthracene-, triptycene-, spirobifluorene-, Tröger's base-, or carbocyclic pseudo-Tröger's base, to form benzodioxane-type PIMs.

Tröger's base is a chiral molecule containing a rigid, V-shaped tertiary amine-based diazocine bridge moiety that has been widely applied in PIMs and PIM-PIs with excellent gas separation performance. Tröger's base formation has also been used to synthesize ladder PIMs (designated TB-PIMs) by reaction of sterically hindered diamines with dimethoxymethane. The overall performance of ladder PIMs for different gas pairs was located close to or above the 2008 gas permeability/selectivity upper bounds. The best performing PIMs even defined the latest 2015 trade-off curves for $O_2/N_2$, $H_2/N_2$ and $H_2/CH_4$ separations.

The gas separation properties of ladder PIMs depend strongly on the rigidity and pore size distribution induced by the internal free volume (IFV) of the contortion centers, such as spirobisindane, ethanoanthracene and triptycene. Most importantly for the generation of highly permeable and selective PIMs it is essential to create a bimodal distribution of microporosity in the polymer containing: a) ultramicropores (<7 Å) that provide bottlenecks for selective gas transport; and b) larger micropores (>10 Å) that generate interconnected pathways for fast gas permeation. Currently, the selection of suitable contortion centers is rather limited.

A known dibenzocyclobutanorbornane structure obtained via catalytic arene-norbornene annulation (referred to herein as a "CANAL" building block) is shown in FIG. 1. The rigid CANAL PIM motif has a W-shaped structure, making this contortion center an excellent candidate for design of highly microporous polymers. Some related ladder PIMs and co-PIMs with modest to high surface area up to ~600 m² g⁻¹ have been reported. However, the first generation of CANAL ladder polymers were too brittle to prepare mechanically strong enough films for gas permeation testing. Therefore, novel sterically hindered monomeric building blocks with high rigidity and well-defined internal free volume are needed for designing and exploring PIMs with more optimized gas separation performance.

SUMMARY

The present disclosure relates to intrinsically microporous ladder-type Tröger's base polymers including a repeat unit based on a combination of a W-shaped CANAL-type building block and a V-shaped Tröger's base building block. Embodiments of intrinsically microporous ladder-type Tröger's base polymers described in the present disclosure possess high BET surface areas, a bimodal pore size distribution with a large fraction of ultramicropores (<7 Å), and excellent thermal, chemical, mechanical, and film-forming properties. The contorted shape of the intrinsically microporous ladder-type Tröger's base polymers described herein ensures microporosity and solubility in solvents, such as chloroform and dichloromethane, and permits casting from solution into robust films useful as highly efficient separation membranes, such as gas separation membranes.

In general, embodiments of the present disclosure feature an intrinsically microporous ladder-type Tröger's base polymer including a repeat unit based on a combination of W-shaped CANAL-type and V-shaped Tröger's base building blocks. Accordingly, embodiments of the present disclosure describe a composition comprising the intrinsically microporous ladder-type Tröger's base polymer comprising a repeat unit with the structure of formula (I):

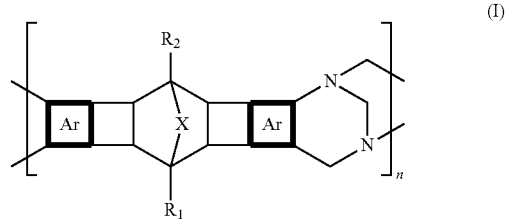

wherein each Ar can be independently selected from unsubstituted and substituted aryl groups; X can be a carbon or heteroatom bridging moiety selected from —[O]—, —[S]—, —[B(O)R$^a$]—, —[NR$^a$]—, —[P(O)R$^a$]—, —[(PO)(O)R$^a$]—, —[CO]—, —[—CR$^a$R$^b$]—, —[C(O)R$^a$(O)R$^b$]—, or —[Si(O)R$^a$(O)R$^b$]—; R$^a$ and R$^b$ can be independently selected from the group consisting of hydrogen, alkyl groups, aryl groups, and heterocyclic groups; R$_1$ and R$_2$ can be independently selected from the group consisting of hydrogen, unsubstituted and substituted, linear or branched alkyl groups, substituted and unsubstituted alkoxy groups, substituted and unsubstituted aryl groups, heterocyclic groups, halogen groups, —CHO, groups having an —O— moiety, groups having an —O(CO)— moiety, groups having an —O(CO)O— moiety, groups having an —O(CO)N< moiety, groups having a —S— moiety, groups having a —B< moiety, —NO$_2$, groups having a —N< moiety, groups having a —P< moiety, groups having a —(PO)< moiety, groups having a —(CO)— moiety, groups having a —(CO)O— moiety, groups having a —(CO)N< moiety and groups having a —Si≡ moiety; and n is an integer greater than 1.

In one or more embodiments, the ladder-type Tröger's base polymer can have a BET surface area (i.e., as characterized by the Brunauer-Emmett-Teller method) greater than about 600 m² g⁻¹. In some cases, the BET surface area is greater than about 600 m²g⁻¹ and less than about 1,000 m²/g, such as from about 700, 750, 800, 850, 880, 890, or from about 975, 985, 990, 995, and up to about 1,000 m²g⁻¹. In one or more of the embodiments above, the intrinsically microporous ladder-type Tröger's base polymer can be thermostable up to about 440° C. ($T_d$, 5% weight loss). In one or more of the embodiments above, X can be a carbon, $R_1$ and $R_2$ can be hydrogen, and each Ar can be independently selected from the group consisting of:

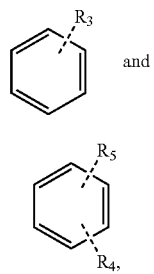

(II) and (III)

wherein, $R_3$, $R_4$, and $R_5$ can be independently selected from the group consisting of linear or branched, unsubstituted or substituted alkyl groups, unsubstituted or substituted alkoxy groups, unsubstituted or substituted unsaturated aliphatic groups, unsubstituted or substituted cycloalkyl groups, unsubstituted or substituted aryl groups, unsubstituted or substituted heterocyclic groups, —CHO, groups having a —O— moiety, groups having a —O(CO)— moiety, groups having a —O(CO)O— moiety), groups having a —O(CO)N< moiety, groups having a —S— moiety, groups having a —B< moiety, —NO₂, groups having a —N< moiety, groups having a —P< moiety, groups having a —PO< moiety, groups having a —(CO)— moiety, groups having a —(CO)O— moiety, groups having a —(CO)N< moiety, and groups having a —Si≡ moiety. In one or more of the embodiments above, n can be greater than 5. For example, n can be greater than 5 and less than 10,000, less than 1,000, or less than 100. In one or more of the embodiments above, the repeat unit has a structure represented by formula (IV) or formula (V):

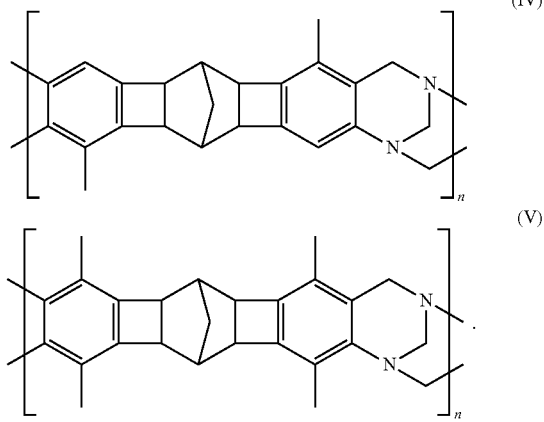

(IV)

(V)

In one or more of the embodiments above, the composition can be configured as (i.e., has the form of) a flat sheet membrane, a rolled flat sheet membrane, a supported membrane, a cylinder, a tube, a capillary, a hollow fiber, or a powder. In one or more embodiments above, the composition can be in the form of a flat sheet membrane having a thickness of about 30 to about 90 μm, and more preferably about 1 to about 30 μm. In one or more of the embodiments above, the intrinsically microporous ladder-type Tröger's base polymer can have a bimodal pore size distribution comprising ultramicropores.

Another embodiment of the present disclosure is a method of synthesizing an intrinsically microporous ladder-type Tröger's base polymer comprising (a) forming a ladder-type diamine monomer by catalytic arene-norbornene annulation (CANAL) polymerization of a halogenated arylamine and norbornadiene or a derivative thereof, wherein the molar ratio of the halogenated arylamine to norbornadiene or the derivative thereof is 2:1, or (a1) forming a first intermediate ladder-type compound by CANAL polymerization of a halogenated arene and norbornadiene or a derivative thereof, wherein the ratio of the halogenated arene to norbornadiene or the derivative thereof is 2:1; (a2) nitrating the first intermediate ladder-type compound to form an intermediate ladder-type dinitro compound; and (a3) reducing the two nitro groups of the intermediate ladder-type dinitro compound to form a ladder-type diamine monomer; and (b) reacting at least two of the ladder-type diamine monomers to form an intrinsically microporous ladder-type Tröger's base polymer comprising a repeat unit represented by formula (I) (above), wherein each Ar can be independently selected from unsubstituted and substituted aryl groups; X can be a carbon or heteroatom bridging moiety selected from —[O]—, —[S]—, —[B(O)Rᵃ]—, —[NRᵃ]—, —[P(O)Rᵃ]—, —[(PO)(O)Rᵃ]—, —[CO]—, —[—CRᵃRᵇ]—, —[C(O)Rᵃ(O)Rᵇ]—, or —[Si(O)Rᵃ(O)Rᵇ]—; $R^a$ and $R^b$ can be independently selected from the group consisting of hydrogen, alkyl groups, aryl groups, and heterocyclic groups; $R_1$ and $R_2$ can be independently selected from the group consisting of hydrogen, unsubstituted and substituted, linear or branched alkyl groups, substituted and unsubstituted alkoxy groups, substituted and unsubstituted aryl groups, heterocyclic groups, halogen groups, —CHO, groups having an —O— moiety, groups having an —O(CO)— moiety, groups having an —O(CO)O— moiety, groups having an —O(CO)N< moiety, groups having a —S— moiety, groups having a —B< moiety, —NO₂, groups having a —N< moiety, groups having a —P< moiety, groups having a —(PO)< moiety, groups having a —(CO)— moiety, groups having a —(CO)O— moiety, groups having a —(CO)N< moiety and groups having a —Si= moiety; and n is an integer greater than 1.

In one or more embodiments, the method comprises performing step (a), wherein the halogenated arylamine has a structure represented by formula (VI):

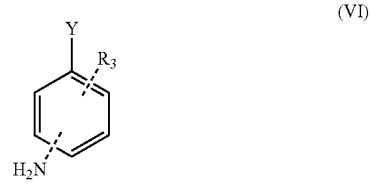

(VI)

Wherein Y can be a chloro, bromo, or iodo group, $R_3$ can be selected from the group consisting of linear or branched unsubstituted or substituted alkyl groups, unsubstituted or substituted unsaturated aliphatic groups, unsubstituted or substituted cycloalkyl groups, unsubstituted or substituted aryl groups, unsubstituted or substituted heterocyclic groups, and unsubstituted or substituted alkoxy groups, —CHO, groups having a —O— moiety, groups having a —O(CO)— moiety, groups having a —O(CO)O— moiety), groups having a —O(CO)N< moiety, groups having a —S— moiety, groups having a —B< moiety, —NO$_2$, groups having a —N< moiety, groups having a —P< moiety, groups having a —PO< moiety, groups having a —(CO)— moiety, groups having a —(CO)O— moiety, groups having a —(CO)N< moiety, and groups having a —Si≡ moiety. In one or more embodiments, the method comprises performing steps (a1)-(a3), wherein the halogenated arene has a structure represented by formula (VII):

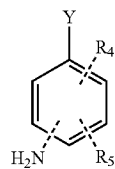

(VII)

wherein Y can be a chloro, bromo, or iodo group, R$_4$ and R$_5$ can be independently selected from the group consisting of linear or branched unsubstituted or substituted alkyl groups, unsubstituted or substituted unsaturated aliphatic groups, unsubstituted or substituted cycloalkyl groups, unsubstituted or substituted aryl groups, unsubstituted or substituted heterocyclic groups, and alkoxy groups, —CHO, groups having a —O— moiety, groups having a —O(CO)— moiety, groups having a —O(CO)O— moiety), groups having a —O(CO)N< moiety, groups having a —S— moiety, groups having a —B< moiety, —NO$_2$, groups having a —N< moiety, groups having a —P< moiety, groups having a —PO< moiety, groups having a —(CO)— moiety, groups having a —(CO)O— moiety, groups having a —(CO)N< moiety, and groups having a —Si≡ moiety. In some cases, nitrating in step (a2) can include contacting the first intermediate ladder-type compound with one or more of potassium nitrate, sulfuric acid, trifluoroacetic anhydride, and nitric acid. In some cases, selectively reducing (in step (a3)) can include catalytic hydrogenation. For example, catalytic hydrogenation can comprise refluxing the intermediate dinitro compound in the presence of hydrazine monohydrate and palladium on carbon. In one or more of the embodiments above, step (b) can comprise reacting the ladder-type diamine monomers with a formaldehyde source and a Lewis acid catalyst. In some cases, the formaldehyde source can be dimethoxymethane and the Lewis acid catalyst can be trifluoroacetic acid.

Embodiments of the present disclosure further include a CANAL-type ladder compound for preparing an intrinsically microporous ladder-type Tröger's base polymer (i.e., comprising a repeat unit with structure of formula (I) above), the CANAL-type ladder compound having a structure represented by formula (VIII):

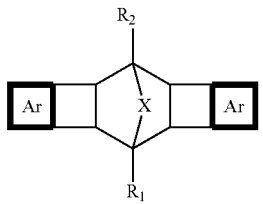

(VIII)

wherein each Ar can be independently selected from unsubstituted or substituted aryl groups, X can be a carbon or heteroatom bridging moiety selected from —[O]—, —[S]—, —[B(O)R$^a$]—, —[NR$^a$]—, —[P(O)R$^a$]—, —[(PO)(O)R$^a$]—, —[CO]—, —[—CR$^a$R$^b$]—, —[C(O)R$^a$(O)R$^b$]—, or —[Si(O)R$^a$(O)R$^b$]—, and R$^a$ and R$^b$ can be independently selected from the group consisting of hydrogen, alkyl groups, aryl groups, and heterocyclic groups, R$_1$ and R$_2$ are independently selected from the group consisting of hydrogen, unsubstituted and substituted, linear or branched alkyl groups, substituted and unsubstituted alkoxy groups, substituted and unsubstituted aryl groups, heterocyclic groups, halogen groups, —CHO, groups having an —O— moiety, groups having an —O(CO)— moiety, groups having an —O(CO)O— moiety, groups having an —O(CO)N< moiety, groups having a —S— moiety, groups having a —B< moiety, —NO$_2$, groups having a —N< moiety, groups having a —P< moiety, groups having a —(PO)< moiety, groups having a —(CO)— moiety, groups having a —(CO)O— moiety, groups having a —(CO)N< moiety and groups having a —Si= moiety. In one or more embodiments, at least one Ar is an arylamine group, such as an aniline group (e.g., a mono- or disubstituted aniline group), X is a carbon, and R$_1$ and R$_2$ are hydrogen. In some embodiments, each Ar can be a m-toluidine (i.e., 3-methylaniline) or p-xylidine (i.e., 2,5-dimethylaniline) moiety. In one or more embodiments, at least one Ar is a nitroarene moiety, such as 2,5-dimethylnitrobenzene. In one or more embodiments, each Ar can be a substituted benzene moiety, such as a dialkyl substituted benzene (e.g., p-xylene).

Another embodiment of the present disclosure is a method using a composition comprising an intrinsically microporous ladder-type Tröger's base polymer as defined above in a method of separating a chemical species in a fluid composition comprising a mixture of at least two chemical species comprising: (a) contacting a membrane comprising an intrinsically microporous ladder-type Tröger's base polymer with a fluid composition comprising at least two chemical species; and (b) separating a first chemical species from the fluid composition; wherein the intrinsically microporous ladder-type Tröger's base polymer comprises a repeat unit represented by formula (I) (above), wherein each Ar is independently selected from an unsubstituted or substituted aryl group; X is a carbon or heteroatom bridging moiety selected from —[O]—, —[S]—, —[B(O)R$^a$]—, —[NR$^a$]—, —[P(O)R$^a$]—, —[(PO)(O)R$^a$]—, —[CO]—, —[—CR$^a$R$^b$]—, —[C(O)R$^a$(O)R$^b$]—, or —[Si(O)R$^a$(O)R$^b$]—, and R$^a$ and R$^b$ are independently selected from the group consisting of hydrogen, alkyl groups, aryl groups, and heterocyclic groups; R$_1$ and R$_2$ are independently selected from the group consisting of hydrogen, unsubstituted and substituted, linear or branched alkyl groups, substituted and unsubstituted alkoxy groups, substituted and unsubstituted aryl groups, heterocyclic groups, halogen groups, —CHO, groups having an —O— moiety, groups having an —O(CO)— moiety, groups having an —O(CO)O— moiety, groups having an —O(CO)N< moiety, groups having a —S— moiety, groups having a —B< moiety, —NO$_2$, groups having a —N< moiety, groups having a —P< moiety, groups having a —(PO)< moiety, groups having a —(CO— moiety, groups having a —(CO)O— moiety, groups having a —(CO)N< moiety and groups having a —Si= moiety; and n is an integer greater than 1. In one or more embodiments of the method, wherein the fluid composition can be selected from the group consisting of air, natural gas, flue gas, ammonia synthesis purge streams, hydrocarbon processing gas, steam reforming gas, gasification process gas, off-gases from refinery or petrochemical plants, and a combination thereof. In one or more embodiments of the method the fluid composition comprises a gaseous chemical species selected from the group consisting of H$_2$, O$_2$, and CO$_2$. In one or more of embodiments of the method, the membrane can be permeable to one or more of H$_2$, O$_2$, and CO$_2$.

The details of one or more examples are set forth in the description below. Other features, objects, and advantages will be apparent from the description and from the claims.

BRIEF DESCRIPTION OF DRAWINGS

This written disclosure describes illustrative embodiments that are non-limiting and non-exhaustive. In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

Reference is made to illustrative embodiments that are depicted in the figures, in which:

FIGS. 9A-B show (A) the N$_2$ adsorption/desorption isotherms of SP-TB-1 and SP-TB-2 at −196° C.; and (B) the pore size distribution of the SP-TB-1 and SP-TB-2 derived from N$_2$ adsorption isotherms by the NLDFT method.

FIGS. 12A-F show structural depictions of two polymer repeat units, according to one or more embodiments of the present disclosure: (A) the SP-TB-1 repeat unit—the upper and lower arcs show dihedral angles between the CANAL and Tröger's base; (B) the optimized geometric single repeat unit of SP-TB-1 from (C)—the methyl group is highlighted as a dashed ring; (C) the optimized geometric SP-TB-1 polymer structure; (D) the structure of the SP-TB-2 repeat unit—the upper and lower arcs show dihedral angles between CANAL and Tröger's base; (E) the optimized geometric single repeat unit of SP-TB-2 from (F)—the methyl group is highlighted as a dashed ring; and (F) the optimized geometric SP-TB-2 polymer structure.

DETAILED DESCRIPTION

Figure 1:
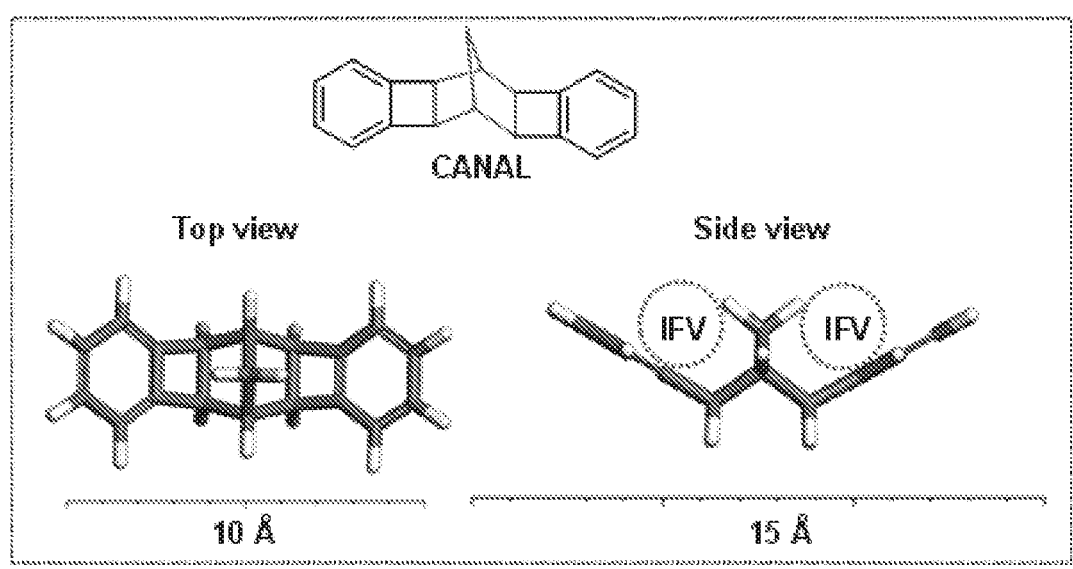
FIG. 1 shows the chemical structure of dibenzocyclobutanorbornane (referred to as "CANAL"), a building block of an intrinsically microporous ladder-type Tröger's base polymer, according to one or more embodiments of the present disclosure, with top and side views of its optimized structures, and the potential internal free volume (IFV) inside the W-shaped site of contortion shown in the center of the building block.

Embodiments of the present disclosure describe intrinsically microporous ladder-type Tröger's base polymers that include a repeat unit based on a combination of W-shaped CANAL-type and V-shaped Tröger's base building blocks, methods of making the intrinsically microporous ladder-type Tröger's base polymer, and methods of using the intrinsically microporous ladder-type Tröger's base polymer to separate a chemical species from a fluid composition including a mixture of chemical species. Embodiments of the present disclosure further describe a repeat unit based on the combination of a W-shaped CANAL-type and a V-shaped Tröger's base building block and methods of making the repeat unit.

Definitions

The terms recited below have been defined as described below. All other terms and phrases in this disclosure shall be construed according to their ordinary meaning as understood by one of skill in the art.

As used herein, "aliphatic" or "aliphatic group" refers to a saturated or unsaturated, linear or branched, cyclic (non-aromatic) or heterocyclic (non-aromatic), hydrocarbon or hydrocarbon group, where each can be substituted or unsubstituted, and encompasses alkyl, alkenyl, and alkynyl groups, and alkanes, alkene, and alkynes, including substituted or unsubstituted groups. An aliphatic group can be monovalent (e.g., —CH$_3$) or multivalent (e.g., bivalent (e.g., —CH$_2$—CH$_2$—)) depending upon the specific structure or formula in which it is used. A multivalent group is one which has two or more carbon-carbon sigma bonds, as compared to one that has only one carbon-carbon sigma bond. In situations where an aliphatic group is used, the number of H present on one or more carbons can be adjusted so that the appropriate bonding scheme can be accomplished (e.g., a carbon may have 3, 2, or 1H in various situations so that the carbon can bond to one, two or three other atoms), where one of skill in the art can determine the appropriate bonding scheme.

As used herein, "alkyl" or "alkyl group" refers to a saturated aliphatic hydrocarbon radical which can be straight or branched, having 1 to 20 carbon atoms, wherein the stated range of carbon atoms includes each intervening integer individually, as well as sub-ranges. An alkyl group can be monovalent (e.g., —CH$_3$) or multivalent (e.g., bivalent, such as —CH$_2$—CH$_2$—) depending upon the specific structure or formula in which it is used. A multivalent group is one which has two or more carbon-carbon sigma bonds, such as a —CH$_2$— or methylene group (i.e., bivalent alkyl group), as compared to a terminal —CH$_3$ (methyl) alkyl group which has only one carbon-carbon sigma bond. Examples of alkyl groups include, but are not limited to methyl, ethyl, n-propyl, iso-propyl, n-butyl, sec-butyl, T-butyl, n-pentyl, iso-pentyl, and sec-pentyl. The term "lower alkyl" means an alkyl group having less than 10 carbon atoms. Reference to an alkyl includes unsubstituted alkyls or substituted alkyls.

As used herein, the term "alkoxy" or "alkoxy group" refers to a functional group and/or substituent with the chemical formula —OR, where R is any alkyl group. Representative alkoxy groups may include, but are not limited to, one or more of methoxy, ethoxy, propoxy, iso-propoxy, butoxy, sec-butoxy, isobutoxy, tert-butoxy, pentoxy, hexoxy, and the like.

As used herein, "ANTB-PIM", refers to an "Arene-Norbornene-Tröger's base-polymer of intrinsic microporosity", according to one or more embodiments of the present disclosure.

As used herein, "arene" or "aromatic group" refers to aromatic monocyclic or multicyclic ring system having 1 to 20 carbon atoms, about 6 to about 14 carbon atoms, or about 8 to about 10 carbon atoms, where the stated range of carbon atoms includes each intervening integer individually, as well as sub-ranges. An aromatic group can be monovalent or multivalent depending upon the specific structure or formula in which it is used. A multivalent group is one which has two or more carbon-carbon sigma bonds, as compared to one that has only one carbon-carbon sigma bond. In situations where an aromatic group is used, the number of H present on one or more carbons can be adjusted so that the appropriate bonding scheme can be accomplished (e.g., a carbon may have 3, 2, or 1H in various situations so that the carbon can bond to one, two or three other atoms), where one of skill in the art can determine the appropriate bonding scheme. An aromatic group can be substituted or unsubstituted.

As used herein, "aryl" refers to a monovalent mono-, bi- or tricyclic aromatic hydrocarbon moiety of 6 to 15 ring atoms, which is optionally substituted with one or more, typically one, two, or three substituents within the ring structure. When two or more substituents are present in an aryl group, each substituent is independently selected. Exemplary aryl includes, but is not limited to, benzene, phenyl, 1-naphthyl, and 2-naphthyl, and the like, each of which can optionally be substituted. The term "aryl" may include heteroaryl or heteroaryl groups. The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures, including furanyl, imidazyl, pyranyl, pyrrolyl, and pyridyl. A heteroaryl can unsubstituted or substituted. In embodiments where a bond is present to the heteroaryl ring, the bond can be to a C or the heteroatom of the ring.

As used herein, "BET", refers to the Brunauer, Emmett, and Teller method for calculating the specific surface area of a sample including the pore size distribution from gas adsorption.

As used herein, "CANAL", refers to the polymer synthesis technique known as catalytic arene-norbornene annulation (CANAL) polymerization and also a building block made by catalytic annulation of two arene-based monomers with a norbornadiene-based monomer. The use of the term CANAL is not intended to limit the arene moiety to a specific aromatic hydrocarbon or the norbornadiene moiety to norbornadiene, and embraces the structure depicted in FIG. 1 and derivatives thereof, as described in the present disclosure.

As used herein, "halogen" or "halide" refers to a fluorine, chlorine, bromine, and iodine, and radicals thereof.

As used herein, the phrase "ladder-type Tröger's base polymer" refers to a polymer having a repeat unit with the structure of formula (I). This phrase is used interchangeably in the Examples with "CANAL-type ladder polymers" Ladder polymers are polymers with backbones of fused rings with adjacent rings having two or more atoms in common.

As used herein, the term "fiber" refers to an elongated structure having a cross-sectional outer diameter in a range of from about 10 micron to about 10 millimeter.

As used herein, the terms "SP-1-TB" and "SP-2-TB" refer to species of intrinsically microporous ladder-type Tröger's base polymer, or membranes cast from solutions of the respective polymer, according to several embodiments of the present disclosure.

The term "substituted" refers to a molecule or functional group in which one or more hydrogen atoms of a designated atom have been replaced by other atom(s) or groups(s), provided that the normal valence of the designated atom is not exceeded. Each independently selected substituent may be the same or different than other substituents. For example, an R group of a formula may be substituted (e.g., from 1 to 4 times)independently with a halogen, hydroxy, acyl, alkyl, alkenyl, alkynyl, cycloalkyl, heterocyclo, aryl, heteroaryl, alkoxy, amino, amide, thiol, sulfone, sulfoxide, oxy, nitro, carbonyl, carboxy, or amino acid. The term "substituted" in, for example, "substituted alkyl", "substituted aryl", "substituted heteroaryl" and the like, means that the substituted group may contain a group such as alkyl, hydroxy, amino, halo, trifluoromethyl, cyano, —NH(alkyl), —N(alkyl)$_2$, alkoxy, alkylthio, or carboxy in place of one or more hydrogens, and includes haloalkyl, alkoxy, fluorobenzyl, and the sulfur and phosphorous containing substitutions. The term "disubstituted" (e.g., in disubstituted arene) refers to a molecule or functional group in which two hydrogen atoms have be replaced.

As used herein, "Tröger's base" refers to any Tröger's base and/or any derivative thereof. The prototype Tröger's base, 2,8-dimethyl-6H,12H-5,11

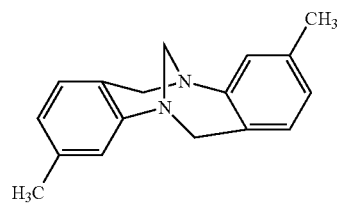 [SMILES: Cc1ccc2c(c1)N1Cc3ccc(C)cc3N(C2)C1]

-methanodibenzo[b,f][1,5]diazocine (CH$_3$C$_6$H$_4$NCH$_2$)$_2$CH$_2$) is a tertiary amine, which exhibits chirality due to the presence of two bridgehead stereogenic nitrogen atoms. It has the general structure:

A Tröger's base derivative may include more functional groups and/or substituents, or less functional groups and/or substituents relative to a Tröger's base on the phenyl rings. The functional groups and/or substituents optionally may be provided at the same or different positions on the phenyl rings relative to the Tröger's base.

Embodiments of the present disclosure feature intrinsically microporous ladder-type Tröger's base polymers and membranes made therefrom, methods of making the ladder-type Tröger's base polymers, including monomeric units and methods of making the monomeric units, as well as methods of using the ladder-type Tröger's base polymers to separate a chemical species from a fluid composition comprising at least two chemical species.

Intrinsically Microporous Ladder-Type Tröger's Base Polymers and Membranes Made Therefrom Embodiments of the present disclosure are directed to an intrinsically microporous ladder-type Tröger's base polymer including a repeat unit based on the combination of W-shaped CANAL-type and V-shaped Tröger's base building blocks, possessing high BET surface area and a large fraction of ultramicropores (<7 Å). Intrinsically microporous ladder-type Tröger's base polymers according to one or more embodiments of the present disclosure exhibit excellent thermal, chemical, mechanical, and film-forming properties, and can be useful as highly efficient gas separation membranes. For example, isotropic films comprising intrinsically microporous ladder-type Tröger's base polymers can exhibit strong molecular sieving properties as a result of the highly contorted and rigid W-shaped and V-shaped building blocks, with high gas permeabilities and good selectivities for smaller gas molecules, such as hydrogen and oxygen, over larger molecules, such as nitrogen.

In some embodiments, an intrinsically microporous ladder-type Tröger's base polymer includes a repeat unit represented by the structure of formula (I),

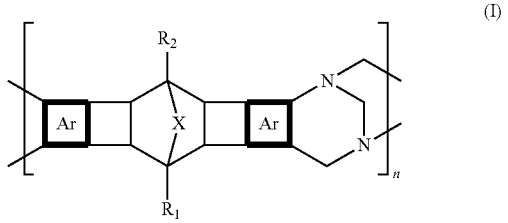

(I)

wherein each Ar can be independently selected from unsubstituted and substituted aryl groups, X can be a carbon or heteroatom bridging moiety selected from —[O]—, —[S]—, —[B(O)R$^a$]—, —[NR$^a$]—, —[P(O)R$^a$]—, —[(PO)(O)R$^a$]—, —[CO]—, —[—CR$^a$R$^b$]—, —[C(O)R$^a$(O)R$^b$]—, or —[Si(O)R$^a$(O)R$^b$]—, R$^a$ and R$^b$ can be independently selected from the group consisting of hydrogen, alkyl groups, aryl groups, and heterocyclic groups; R$_1$ and R$_2$ can be independently selected from the group consisting of hydrogen, unsubstituted and substituted, linear or branched alkyl groups, substituted and unsubstituted alkoxy groups, substituted and unsubstituted aryl groups, heterocyclic groups, halogen groups, —CHO, groups having an —O— moiety, groups having an —O(CO)— moiety, groups having an —O(CO)O— moiety, groups having an —O(CO)N< moiety, groups having a —S— moiety, groups having a —B< moiety, —NO$_2$, groups having a —N< moiety, groups having a —P< moiety, groups having a —(PO)< moiety, groups having a —(CO)— moiety, groups having a —(CO)O— moiety, groups having a —(CO)N< moiety and groups having a —Si≡ moiety; n is an integer greater than 1. For example, the number of repeat units (n) can be any integer within the range of 2 to 10,000, such as 5, 6, 7, 8, 9, 10 . . . 100 . . . , 1,000 . . . and up to 10,000. Repeat units can be forcefield-optimized using a smart algorithm with ultra-fine convergence (e.g. COMPASS (Condensed-phase Optimized Molecular Potentials for Atomistic Simulation Studies)). Polymers with different repeat unit lengths (e.g., 6 and 7) can be synthesized based on the growth of the optimized repeat unit. The relative configurations defined by the bridging methylene groups in the Tröger's base (e.g., syn and anti) can be arranged randomly along the polymer backbones.

In one or more of the embodiments above, X can be a carbon, R$_1$ and R$_2$ can be hydrogen, and each Ar can be independently selected from the group consisting of substituted benzenes as represented by structures (II) and (III):

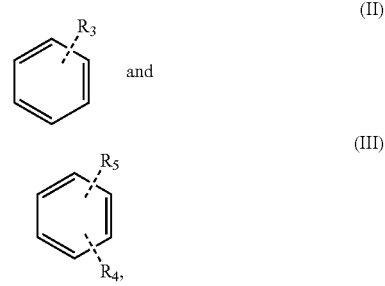

wherein, each of R$_3$, R$_4$, and R$_5$ can be independently selected from the group consisting of linear or branched, unsubstituted or substituted alkyl groups, linear or branched, unsubstituted or substituted alkoxy groups, unsubstituted or substituted unsaturated aliphatic groups, unsubstituted or substituted cycloalkyl groups, unsubstituted or substituted aryl groups, unsubstituted or substituted heterocyclic groups, —CHO, groups having a —O— moiety, groups having a —O(CO)— moiety, groups having a —O(CO)O— moiety), groups having a —O(CO)N< moiety, groups having a —S— moiety, groups having a —B< moiety, —NO$_2$, groups having a —N< moiety, groups having a —P< moiety, groups having a —PO< moiety, groups having a —(CO)— moiety, groups having a —(CO)O— moiety, groups having a —(CO)N< moiety, and groups having a —Si≡ moiety.

In one or more of the embodiments above, the intrinsically microporous ladder-type Tröger's base polymer can include a repeat unit as represented by formula (IV) (e.g., having a repeat unit as described for SP-TB-1) and (V) (e.g., having a repeat unit as described for SP-TB-2):

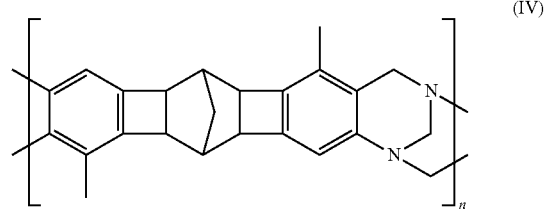

(IV)

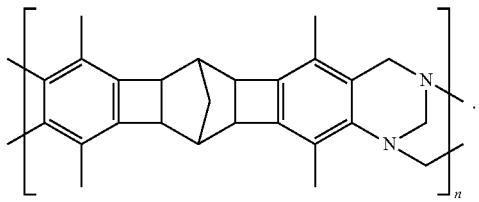

(V)

Intrinsically microporous ladder-type Tröger's base polymers as described above can be organosoluble (i.e., solution processable). For example, intrinsically microporous ladder-type Tröger's base polymers of the present disclosure can be soluble in solvents such as chloroform, dichloromethane, tetrahydrofuran, toluene, or chlorobenzene. The polymers can be purified from the polymerization reaction mixture to remove oligomers and residual solvent by re-precipitation of the polymer from solution using a nonsolvent. Solidified polymer (e.g., powders or films) can be treated with non-solvent (e.g., methanol and/or ethanol) to remove residual solvent or to condition the polymer.

The present disclosure features a composition comprising an intrinsically microporous ladder-type Tröger's base polymer including a repeat unit of formula (I). The composition can be flowable (e.g., a solution comprising dissolved polymer or a suspension of precipitated polymer) or solid. The composition can include a solvent and/or non-solvent. The composition can include a blend of two or more intrinsically microporous ladder-type Tröger's base polymers, or a blend of an intrinsically microporous ladder-type Tröger's base polymer and one or more of other polymers (e.g., a polymer of intrinsic microporosity (PIMs), porous organic polymers (POPs), polymeric fillers/plasticizers), metal organic frameworks (MOFs), porogens, zeolites or fillers. In some cases, the composition includes a single species of intrinsically microporous ladder-type Tröger's base polymer, such as a homopolymer having a repeating unit of formula (IV) or formula (V).

In one or more embodiments, the composition is configured to have a form suitable for its intended use. In some cases, the composition comprising an intrinsically microporous ladder-type Tröger's base polymer including the repeat unit of formula (I) can be configured as (i.e., has the form of) a free-standing membrane, a flat sheet membrane, a rolled (e.g., to form spirals) flat sheet membrane, a supported membrane (e.g., a composite membrane with a polymer layer on a permeable cloth or a screen), a dense film, a coated film, a coating, a cylinder, a tube, a capillary, a hollow fiber (including a composite fiber), a bead, or a powder. For example, to determine the physical and mechanical properties of the polymer, the composition may be in the form of a dried film, or for gas separations or adsorption, catalysis, or electrochemical applications the composition can be in the form of a membrane. The composition can be characterized as being uniform in all directions (e.g., an isotropic film or membrane), or the composition can vary in one or more directions (e.g. an asymmetric film or membrane).

Films, coatings, and membranes can have a thickness on the scale of nanometers (e.g., ultrathin membranes) to centimeters, or more, depending upon the application. For example, the film, coating or membrane thickness can be within the range of 0.1-100 microns, such as about 0.5, 10, 30, 40, 50, 60, 70, 80, 90 or 100 microns. In some cases, a membrane is greater than 100 microns thick, such as within the range of 50-500 microns. In one or more embodiments of the present disclosure, the composition can be in the form of a multi-layered article. The thickness of an individual layer can vary from about 1% or less to about 99% of the overall article thickness, such as from 10 to 90% of the article thickness. For example, a layer of intrinsically microporous ladder-type Tröger's base polymer can be from 1 micrometer thick or less to about 150 micrometers thick and be supported by or sandwiched between layers of non-porous material or material that are thin, thicker, or the same thickness as the intrinsically microporous ladder-type Tröger's base polymer layer.

Cylindrical membranes can be characterized by the inner diameter, membrane wall thickness, and outer diameter of the cylinder. In some cases, a hollow fiber membrane can have an outer diameter of less than 0.5 mm, capillary membranes have a diameter of 0.5-5 mm, and tubular membranes can have a diameter greater than 5 mm. In some cases, a hollow fiber membrane for gas separation can be symmetric or asymmetric. For example, an asymmetric hollow fiber separation membrane can be a composite membrane. A hollow fiber separation membrane can have a membrane thickness (wall thickness) of 10 to 500 μm, and inner diameter of about 0.1-300 microns and an outer diameter of 50 to 2000 sm.

In one or more embodiments of the present disclosure, the solubility of the intrinsically microporous ladder-type Tröger's base polymer including the repeat unit of formula (I) permits casting into a form suitable for the intended application. For example, the polymer can be dissolved in a solvent and the solubilized polymer composition can be cast to provide the desired configuration. In some cases, the solubilized polymer composition can be filtered before casting. For example, an intrinsically microporous ladder-type Tröger's base polymer can be dissolved in a solvent such as chloroform (e.g., at a concentration of about 2-3% (v/w)), filtered, and cast as a thin film on a support. Alternatively, a liquid composition including polymer in a solvent can be heated to facilitate dissolution of the polymer and the heated solution can be cast (e.g., onto a moving belt) and subjected to cooling. In some cases, the dissolved polymer can be spread (e.g., onto a moving belt) and immersed in a bath of liquid in which the liquid within the bath exchanges with the solvent and causes precipitation of the polymer. In some cases, the dissolved polymer composition can be placed in a vapor atmosphere containing a nonsolvent saturated with the solvent. In some cases, the polymer can be dissolved in a mixture of solvent and nonsolvent, and the higher volatility of the solvent can result in an increasing content of nonsolvent and polymer, thereby causing precipitation of the polymer and formation of a skinned membrane.

Casting generally refers to disposing a material on, in, or around an object or mold, among other things. Casting may include, but is not limited to, one or more of depositing, pouring, dipping, coating, and applying. In many embodiments, casting may refer to disposing a solution on a substrate. The substrate may include any suitable substrate, such as glass, oxide (e.g., alumina), porous substrates, woven or non-woven textiles, and hollow fibers.

After casting, the casting solvent can be removed. Removing the casting solvent generally refers to one or more of drying, heating, evaporating, washing, and any other method known in the art for removing solvent. For example, the dissolved polymer solution can be passed under a series of air flow ducts that control the evaporation of the solvents in a particular set period of time such as 24 to 48 hours. The casting solvent can be removed by slow evaporation at ambient or room temperature (e.g., about 20°

C.), or evaporation under elevated temperature under vacuum. In one or more embodiments, removing includes drying at about ambient or room temperature for at least about 10 hours, at least about 20 hours, at least about 30 hours, or, for at least about 40 hours. In one or more embodiments, removing the solvent generally includes drying or evaporating sufficient to substantially or completely remove solvent. Removing can include drying until a transparent film is obtained. In some cases, the rate of removal can be controlled by covering the mold or support comprising the polymer solution (e.g., with a Petri dish).

In one or more embodiments, removing includes treating the dried composition with a nonsolvent to remove residual solvent and/or to condition the polymer. Treating can include soaking the dried composition in nonsolvent for at least one hour, such as at least 2, 3, or 4 hours. For example, the dried composition can be soaked in methanol for about 4 hours. In some cases, the nonsolvent can be removed by air-drying (e.g., slow evaporation) for at least about 20 hours, at least about 30 hours, at least about 40, or about 50 hours, or by drying under a vacuum at an elevated temperature. For example, the nonsolvent-treated composition can be dried in a vacuum oven at about 120° C. for about 24 hours. The removal of the residual solvent or other volatiles can be verified by thermogravimetric analysis.

In one or more embodiments of the present disclosure, a membrane can be formed by spinning. For example, an intrinsically microporous ladder-type Tröger's base polymer can be dissolved in solvent to produce a spinning dope. The spinning dope can be extruded from a spinneret or syringe to produce a fiber. For example, a hollow fiber membrane can be produced by phase inversion technique from an annular spinneret. Extruded fibers can be used to form non-woven fibrous mats, for example. Residual solvent can be removed from the extruded product as described above for cast forms.

An intrinsically microporous ladder-type Tröger's base polymer including the repeat unit of formula (I) can exhibit a total available pore volume greater than about 0.60 cc g$^{-1}$, such as a pore volume within the range of 0.61-0.7 cc g$^{-1}$. A solid composition comprising an intrinsically microporous ladder-type Tröger's base polymer can be characterized by determining the pore size distribution. In some cases, the solid is characterized as exhibiting a plurality of micropores and a plurality of ultra-micropores. The porous nature of the intrinsically microporous ladder-type Tröger's base polymer can be characterized by analyzing a film or membrane comprising the polymer. For example, a membrane according to one or more embodiments of the present disclosure can exhibit a tight and highly interconnected microporous structure which can be elucidated using low pressure nitrogen adsorption isotherms. The physisorption isotherm (e.g., $N_2$ isotherms at 77 K) and pore size distribution of an intrinsically microporous ladder-type Tröger's base polymer of the present disclosure can be analyzed using the BET Surface Area test.

The pore size distribution can be a good indication for the potential of an intrinsically microporous ladder-type Tröger's base polymer including the repeat unit of formula (I) to achieve the molecular sieving properties associated with high gas-pair selectivity. An interconnected microstructure can indicate transport dominated by diffusion and/or suggest high permeability and high selectivity for gas pairs separations such as $O_2/N_2$, $H_2/N_2$ and $H_2/CH_4$ separations. A solid composition (e.g., membrane or film) comprising an intrinsically microporous ladder-type Tröger's base polymer of the present disclosure can exhibit pores having a pore size (e.g., width) indicative of ultra-microporosity (e.g., less than about 7 Å). The basis for transport dominated by diffusion and the high permeability with high selectivity for important commercial gas pairs separations, such as $O_2/N_2$, $H_2/N_2$ and $H_2/CH_4$ is conferred by an interconnected microstructure tightened with pore size smaller than 7 Å.

In some cases, the pore size distribution (pore width v. dV/dW (cm$^3$ g$^{-1}$)) of an intrinsically microporous ladder-type Tröger's base polymer including the repeat unit of formula (I) has a multimodal distribution. In some cases, the pore size distribution includes one or more populations of pores greater than 10, 11, 12, 13, 14, or 15 Å and one or more populations of pores less than 8, 7, 6, 5, or 4 Å. The pore size distribution can show a larger fraction of ultra-micropores than micropores. For example, the distribution can show a population of pores having a width ≤about 7 Å that is greater than the population of pores having a width ≥about 10 Å.

An intrinsically microporous ladder-type Tröger's base polymer including the repeat unit of formula (I) can have structure that prevents close packing of the components resulting in a BET surface area that can be greater than about 600 m$^2$ g$^{-1}$. In some cases, the BET surface area is greater than about 600 m$^2$g$^{-1}$ and less than about 1,100 m$^2$g$^{-1}$ such as a surface area of greater than 620, 650, 680, 700, 720, 740, 760, 780, 800, 810, 820, 830, 840, 850, 860, 870, 880, 890, 900, and up to about 1,000 m$^2$g$^{-1}$. In some cases, the ladder-type Tröger's base polymer exhibits a BET surface area of about 881 m$^2$g$^{-1}$ or about 987 m$^2$g$^{-1}$. The surface area is conferred by the combination of the W-shaped CANAL building block and the V-shaped Tröger's base building block. Accordingly, an intrinsically microporous ladder-type Tröger's base polymer of one or more embodiments of the present disclosure can exhibit increased surface area relative to a polymer with a Tröger's base motif but lacking an arene-norbornene-based building block.

Intrinsically microporous ladder-type Tröger's base polymers including the repeat unit of formula (I) can exhibit excellent thermal stability. The thermal stability of a polymer can be characterized by Thermal Gravimetric Analysis (TGA). For example, the thermal stability of a polymer film sample can be assessed using a TA Instruments Q5000 sample processor (New Castle, Del.). In some cases, the intrinsically microporous ladder-type Tröger's base polymer exhibits sufficient thermal stability for the polymer to be utilized in a wide range of applications, including high temperature applications (e.g., gas storage). For example, an intrinsically microporous ladder-type Tröger's base polymer can be thermostable above 250° C. In some cases, an intrinsically microporous ladder-type Tröger's base polymer of the present disclosure can exhibit size (weight) stability at temperatures within the range of greater than 250° C. up to about 440° C. In some cases, the 5% weight loss decomposition temperature ($T_{d,5\%}$) is greater than about 300, 325, 350, or about 440° C. Thermostability can also be demonstrated by observing the glass-liquid transition of the intrinsically microporous ladder-type Tröger's base polymer (e.g., by DSC scan). In some cases, the intrinsically microporous ladder-type Tröger's base polymer is a glassy polymer that does not exhibit a glass transition temperature ($T_g$) at temperatures up to about 350° C. Thermal stability can also be demonstrated by the pyrolysis behavior of the polymer. For example, the charcoal content after pyrolysis at 800° C. under inert atmosphere can be measured as an indication of mass retention. In one or more of the embodiments of the present disclosure, a membrane comprising an intrinsically microporous ladder-type Tröger's base polymer can exhibit a char, or charcoal, content of greater than 60%, such as greater than 62% to about 75%. For example, the charcoal content after pyrolysis can be about 64% or about 76%.

In one or more embodiments of the present disclosure, an intrinsically microporous ladder-type Tröger's base polymer including the repeat unit of formula (I) exhibits good mechanical properties for separation applications. For example, a composition comprising an intrinsically microporous ladder-type Tröger's base polymer can be cast to form flexible and mechanically robust films for gas and/or liquid separation applications. The compositions comprising the polymer can be characterized as possessing tensile strength, Young's modulus, and elongation at break sufficient for utility in applications requiring elastic deformation (e.g., high-pressure applications). In some cases, the tensile strength of a film or membrane comprising an intrinsically microporous ladder-type Tröger's base polymer is greater than about 40 MPa, such as greater than about 45, 50, 55, 60, or 63 MPa. For example, the tensile strength can be within the range of about 45-64 MPa. In some cases, the Young's modulus of a film or membrane comprising an intrinsically microporous ladder-type Tröger's base polymer is greater than about 0.4 GPa, such as greater than about 0.5, 1.0, 1.5, or 1.6 GPa. For example, the tensile strength can be within the range of about 0.4-1.65 MPa. In some cases, the elongation at break of a film or membrane comprising an intrinsically microporous ladder-type Tröger's base polymer is greater than about 14%, such as greater than about 14.5, 19.5, 24.5, or 27%. For example, the elongation at break can be within the range of about 14-29%. In some cases, a film or membrane comprising an intrinsically microporous ladder-type Tröger's base polymer can exhibit a combination of mechanical properties within these ranges (e.g., a Young's modulus greater than about 63 MPa, a tensile strength greater than about 1.6 GPa, and an elongation at break of greater than about 27%). In some cases, the mechanical properties of the film or membrane can be manipulated by selection of the solvent or solvent mixture used for casting and/or the process by which the composition is formed (e.g., how the composition is dried). In some cases, treatment or conditioning of the film or membrane (e.g., with methanol) can permit membranes prepared by different methods to be compared during analysis of physical and/or mechanical properties.

In one or more embodiments of the present disclosure, an intrinsically microporous ladder-type Tröger's base polymer including the repeat unit of formula (I) has potential for gas separation applications. High BET surface area polymers of the present disclosure can exhibit unusual vapor/gas mixed-gas permeation properties resulting from the high excess free volume, interconnectivity of free volume elements and large chain spacing. Generally, gas transport properties for membranes can be assessed using a constant volume/variable pressure method or a constant pressure/variable volume method.

Gas separation properties of polymer membrane materials follow distinct tradeoff relations: more permeable polymers are generally less selective and vice versa. Accordingly, a membrane composition comprising an intrinsically microporous ladder-type Tröger's base polymer including the repeat unit of formula (I) can be characterized by its gas permeation and selectivity properties as demonstrated by pure-gas and mixed gas measurements. The performance of polymer membranes for gas separation can be evaluated using Robeson trade-off curves (e.g., 1991, 2008) and the 2015 redefined upper bond. Pure-gas measurements can determine the permeation of $H_2$, $N_2$, $O_2$, $CH_4$, $CO_2$, $C_2H_6$ and $C_3H_8$, for example. In one or more embodiments of the present disclosure, a membrane of the present disclosure exhibits greater hydrogen permeability than carbon dioxide permeability, oxygen permeability greater than methane or nitrogen permeability. For example, a membrane composition can exhibit a sequence of permeability of $PH_2 > PCO_2 > PO_2 > PCH_4 > PN_2$. Mixed-gas measurements can determine the selectivity of the membrane using binary mixtures and ternary mixtures. For example, mixed gas experiments can include $O_2/N_2$, $CO_2/CH_4$, $H_2/N_2$, $He/N_2$, $H_2/CH_4$, $He/CH_4$, $He/H_2$, $H_2/CO_2$, $He/CO_2$, $CO_2/N_2$, $N_2/CH_4$, $C_2H_4/C_2H_6$, and $C_2H_6/C_3H_8$ gas pairs.

In one or more embodiments, a membrane comprising an intrinsically microporous ladder-type Tröger's base polymer including the repeat unit of formula (I) exhibits high permeability (e.g., permeability above the 2008 tradeoff curve the respective gas) for one or more of $H_2$, $O_2$, and $CO_2$ and has high selectivity for one or more binary gas mixtures selected from $H_2/N_2$, $H_2/CH_4$, and $O_2/N_2$ (e.g., selectivity above the 2008 tradeoff curve for the respective pair). For example, high permeability can be shown by determining the moles of gas that would occupy one cubic centimeter of the membrane at standard temperature and pressure, as calculated via the ideal gas law (i.e., $(10^{-10}$ cm$^3$ (STP)·cm)/ (cm$^2$·s·cmHg)=1 Barrer). In some cases, a membrane comprising an intrinsically microporous ladder-type Tröger's base polymer including the repeat unit of formula (I) exhibits a $H_2$ gas permeability of greater than about 1000, 1500, 2000, 2500, and 3000 barrer at 35° C. and 2 bar pressure. For example, the $H_2$ gas permeability at 35° C. and 2 bar can be about 3600 barrer. In some cases, a membrane comprising an intrinsically microporous ladder-type Tröger's base polymer including the repeat unit of formula (I) exhibits an $O_2$ gas permeability of greater than about 200, 300, 400, 500, 600, 700 and 800 barrer at 35° C. and 2 bar. For example, the $O_2$ gas permeability at 35° C. and 2 bar can be about 750 barrer. In some cases, a membrane comprising an intrinsically microporous ladder-type Tröger's base polymer including the repeat unit of formula (I) exhibits a $CO_2$ gas permeability of greater than about 500, 1000, 1500, 2000, 2500, and 3000 barrer at 35° C. and 2 bar. For example, the $CO_2$ gas permeability at 35° C. and 2 bar can be about 2520 barrer. In one or more embodiments, a membrane comprising an intrinsically microporous ladder-type Tröger's base polymer including the repeat unit of formula (I) exhibits a combination of these permeabilities. For example, the $H_2$, $O_2$, and $CO_2$ gas permeability of a membrane can be greater than about 3600, 750, and 2520 barrer, respectively, at 35° C. and 2 bar.

In some cases, a membrane comprising an intrinsically microporous ladder-type Tröger's base polymer including the repeat unit of formula (I) exhibits ideal selectivity ($\alpha_{X/Y}$) for $H_2N_2$, greater than about 15, 20, 25, or 30. For example, the ideal selectivity for $H_2/N_2$ can be about 30. In some cases, a membrane comprising an intrinsically microporous ladder-type Tröger's base polymer including the repeat unit of formula (I) exhibits an ideal selectivity ($\alpha_{X/Y}$) for $H_2/CH_4$, greater than about 10, 15, 20 or 25. For example, the ideal selectivity for $H_2/CH_4$, can be about 22. In some cases, a membrane comprising an intrinsically microporous ladder-type Tröger's base polymer including the repeat unit of formula (I) exhibits ideal selectivity ($\alpha_{X/Y}$) for $O_2N_2$, greater than about 4.0, 4.5, 5.0, or 5.5. For example, the $O_2N_2$, ideal selectivity can be about 5.2. In one or more embodiments, a membrane comprising an intrinsically microporous ladder-type Tröger's base polymer including the repeat unit of formula (I) exhibits a combination of these selectivities. For example, the $H_2/N_2$, $H_2/CH_4$, and $O_2/N_2$ gas selectivity of a membrane can be greater than about 30, 22, and 5.2, respectively, at 35° C. and 2 bar.

The gas transport properties of a membrane can be determined using membranes that have been subjected to different treatments and/or membranes of different thicknesses (e.g., thin membranes (~40 μm) v. thicker membranes). For example, the permeability and selectivity can be determined using membranes prepared by a specific method (e.g., phase-inversion membranes, air-dried membranes, oven dried membranes, and physically aged membranes). In some cases, the permeability and/or selectivity of a membrane can change due to physical aging as a result of non-equilibrium material changing over time towards an equilibrium state. The chains of a glassy polymer can slowly relax and converge, thereby reducing the membrane performance. Accordingly, determining the gas transport properties of a physically aged membrane can provide a means of predicting long-term performance. In some cases, the membrane as described above can be aged more than 3 days, such as more than 5, 10, 50, 100, 300 or 500 days and then analyzed for age-related changes in gas transport properties.

Methods of Preparing an Intrinsically Microporous Ladder-Type Tröger's Base Polymer The present disclosure features methods of making an intrinsically microporous ladder-type Tröger's base polymer. In one or more embodiments described in the present disclosure an intrinsically microporous ladder-type Tröger's base polymer can be made by reacting at least two ladder-type diamine monomers under conditions sufficient for in situ formation of a Tröger's base. In one or more embodiments of the present disclosure, a method of making an intrinsically microporous ladder-type Tröger's base polymer includes synthesizing at least two ladder-type diamine monomers, or an intermediate thereof, by catalytic annulation.

Figure 2:
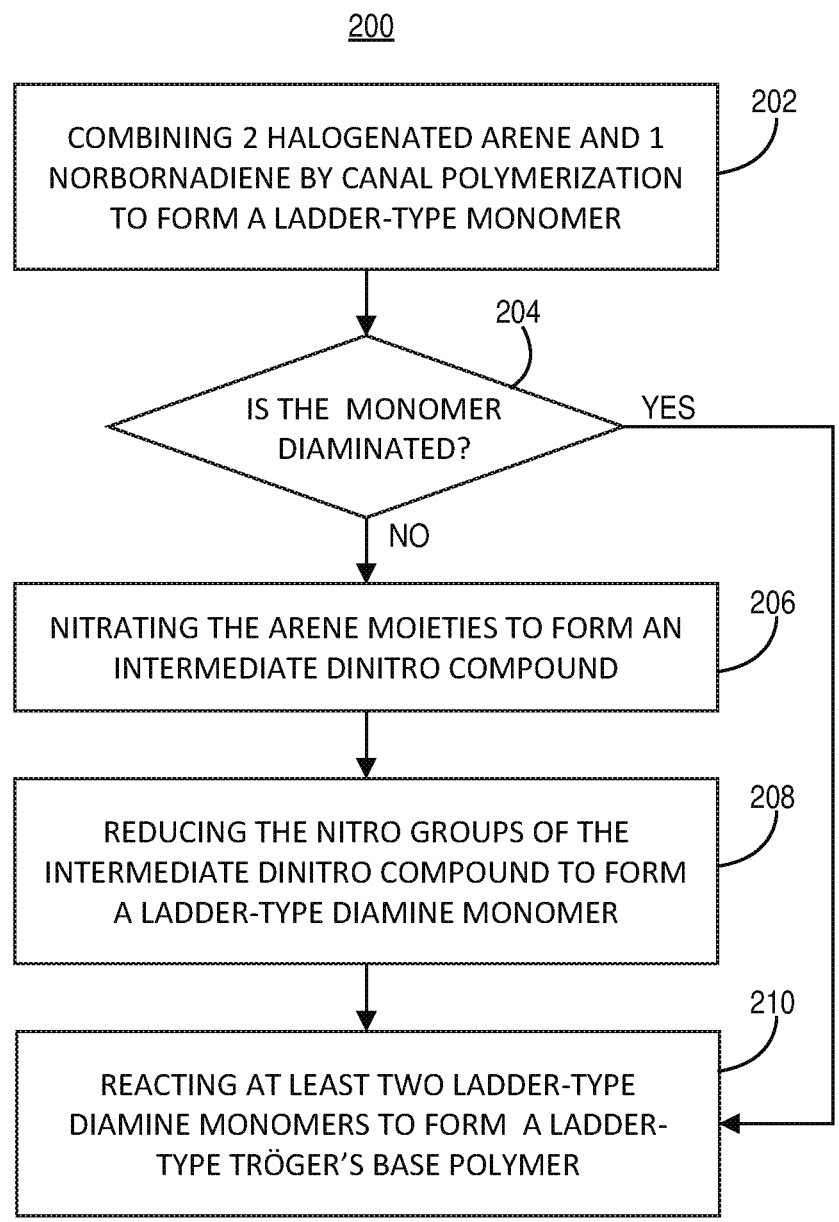
FIG. 2 is a flowchart of a method of making an intrinsically microporous ladder-type Tröger's base polymer, according to one or more embodiments of the present disclosure.

FIG. 2 features method 200 encompassing one or more steps for synthesizing an intrinsically microporous ladder-type Tröger's base polymer comprising a repeat unit with the structure represented by formula (I). In block 202, method 200 includes combining two molar equivalents of a halogenated arene and one molar equivalent of norbornadiene (e.g., (1s,4s)-bicyclo[2.2.1]hepta-2,5-diene) or a derivative thereof using catalytic arene-norbornene annulation (CANAL) polymerization. The reaction product of CANAL polymerization is an unsubstituted or substituted norbornyl diarylcyclobutene-based compound referred to herein as a ladder-type monomer. The reaction product can be a pure isomer or a mixture of isomers.

The halogenated arene can be an aromatic hydrocarbon with at least one halide substitution and one or more additional substitutions. As used herein, the term "halide" refers to one or more of fluoro, chloro, bromo, and iodo groups (e.g., a bromine substituted aromatic hydrocarbon). Aromatic hydrocarbons include monocyclic, bicyclic, tricyclic, and higher order polycyclic), and heterocyclic compounds. The halogenated arene can be further substituted with one or more functional groups including aliphatic, alkyl, cycloalkyl, alcohol, nitro, amine, amide, nitrile, ester, carbamate, carboxylic acid, acid halide, ketone, aldehyde, acid anhydride, thio, sulfide, azide, phosphate, silicone, and heterocycle groups. For example, the halogenated arene can be a substituted bromobenzene represented by the structures of formula (VI) or (VII):

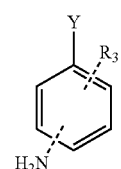

(VI)

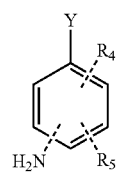

(VII)

wherein Y can be a chloro, bromo, or iodo group, each of $R_3$, $R_4$, and $R_5$ are independently selected from the group consisting of unsubstituted and substituted, linear and branched alkyl groups, unsubstituted and substituted alkoxy groups, unsubstituted and substituted aryl groups, unsubstituted and substituted heterocyclic groups, halogen groups, —CHO, groups including an —O— moiety, groups including an —O(CO)— moiety, groups including an —O(CO)O— moiety, groups including an —O(CO)N< moiety, groups including a —S— moiety, groups including a —B< moiety, —NO$_2$, groups including a —N< moiety, groups including a —P< moiety, groups including a —(PO)< moiety, groups including a —(CO)— moiety, groups including a —(CO)O— moiety, groups including a —(CO)N< moiety and groups including a —Si= moiety. In one or more embodiments, each of $R_3$, $R_4$, and $R_5$ can be independently selected from the group consisting of linear or branched unsubstituted or substituted alkyl groups, unsubstituted or substituted unsaturated aliphatic groups, unsubstituted or substituted cycloalkyl groups, unsubstituted or substituted aryl groups, unsubstituted or substituted heterocyclic groups, and unsubstituted or substituted alkoxy groups. For example, $R_3$, $R_4$, and $R_5$ can be selected from the group consisting of linear or branched unsubstituted or substituted lower alkyl groups, such as methyl, ethyl, n-propyl, iso-propyl, n-butyl, sec-butyl, T-butyl, n-pentyl, iso-pentyl, and sec-pentyl groups. In one or more of the embodiments above, the halogenated arene can be 4-bromo-3-methylaniline, 2-bromo-1,4-dimethylbenzene, or a combination thereof.

In one or more embodiments of method 200, the halogenated arene is combined (polymerized or otherwise reacted) with norbornadiene or a derivative thereof selected from compounds having a structure represented by formula (VIII):

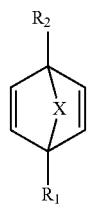

(VIII)

wherein X is a carbon or heteroatom bridging moiety selected from —[O]—, —[S]—, —[B(O)R$^a$]—, —[NR$^a$]—, —[P(O)R$^a$]—, —[(PO)(O)R$^a$]—, —[CO]—, —[—CR$^a$R$^b$]—, —[C(O)R$^a$(O)R$^b$]—, or —[Si(O)R$^a$(O)R$^b$]—, and R$^a$ and R$^b$ are independently selected from the group consisting of hydrogen, alkyl groups, aryl groups, and heterocyclic groups, R$_1$ and R$_2$ are independently selected from the group consisting of hydrogen, unsubstituted and substituted, linear or branched alkyl groups, substituted and unsubstituted alkoxy groups, substituted and unsubstituted aryl groups, heterocyclic groups, halogen groups, —CHO, groups having an —O— moiety, groups having an —O(CO)— moiety, groups having an —O(CO)O— moiety, groups having an —O(CO)N< moiety, groups having a —S— moiety, groups having a —B< moiety, —NO$_2$, groups having a —N< moiety, groups having a —P< moiety, groups having a —(PO)< moiety, groups having a —(CO)— moiety, groups having a —(CO)O— moiety, groups having a —(CO)N< moiety and groups having a —Si═ moiety.

In one or more embodiments of method 200, forming a ladder-type monomer includes polymerizing or otherwise reacting two equivalents of the halogenated arene and one equivalent of norbornadiene or a derivative thereof in an organic solvent, in the presence of a metal catalyst, a ligand, and optionally, an organic or inorganic base (i.e., alkaline substance). A suitable organic solvent can be selected based on its ability to solubilize the halogenated arene and norbornadiene or the derivative thereof. In some cases, the organic solvent can be selected from non-polar organic solvent, such as benzene, alkylbenzenes (e.g., toluene, xylene, and mesitylene), long-chain hydrocarbons (e.g., octane), ethyl acetate, or combinations thereof. In some embodiments, the solvent is an aprotic polar organic solvent, such as 1,4-dioxane, chloroform, N,N-dimethylacetamide (DMAc), NN-dimethylformamide (DMF), dimethylsulfoxide (DMSO), N-methylpyrrolidinone (NMP), sulfolane, diphenylsulfone, or combinations thereof. In some embodiments, a non-polar solvent is used in addition to an aprotic polar solvent. For example, a non-polar solvent can facilitate solubilization of the ladder-type monomer in addition to solubilizing the halogenated arene and norbornadiene or derivative thereof during the reaction. In one or more embodiments of method 200 the solvent used in step 202 is 1,4-dioxane.

A suitable metal catalyst for use in step 202 can be a transition metal catalyst. In some embodiments, the transition metal catalyst is a palladium containing catalyst or a nickel-containing catalyst. Palladium can be in various forms of Pd(0) (elemental form such as Pd on a support) or Pd(II), such as palladium-containing organic complexes (e.g., Pd(OAc)$_2$, PEPPSI™-IPr catalyst, Pd(PPh$_3$)$_4$). Nickel can be in various forms of Ni(0) (elemental nickel) or Ni(II), such as such as nickel-containing organic complexes. A Ni-catalyzed reaction can further contain a reducing agent. In some embodiments, the metal catalyst is another transition metal catalyst or a combination of different transition metal catalysts, such as selected from Groups 3, 4, 5, 6, 7, 8, 9, 10, 11, and 12 of the Periodic Table. In one or more embodiments of method 200, the metal catalyst for catalyzing the ladder-type monomer formation is a palladium containing catalyst selected from Pd on carbon or other support (e.g., granular alumina) and Pd(OAc)$_2$. The catalyst can be present at about 0.9-10 mol %.

A suitable ligand for use in step 202 can be a selected from phosphorus-containing organic ligands, nitrogen-containing organic ligands, and carbon-containing (or -based) ligands. Examples of suitable ligands include phosphines, such as triphenylphosphine (PPh$_3$), tricyclohexylphosphine (PCy$_3$), tritertbutylphosphine (PtBu$_3$), tri(o-tolyl)phosphine (P(o-Tol)$_3$), N-heterocyclic carbine (NHC), or a combination thereof. The ligand can be present at about 2-25 mol %. In one or more embodiments of method 200, the ligand used in step 202 is the ladder-type monomer formation is triphenylphosphine.

A suitable organic or inorganic base for use in step 202 can be selected based upon the compatibility of the base for the catalyst and/or functional groups on the reactants. Examples of suitable bases include aprotic bases such as cesium carbonate (Cs$_2$CO$_3$), potassium carbonate (K$_2$CO$_3$), sodium carbonate (Na$_2$CO$_3$), sodium fluoride (NaF), potassium fluoride (KF), or combinations thereof. Protic bases, such as sodium hydroxide (NaOH), potassium hydroxide (KOH), or combinations thereof, also can be suitable bases, for example, if the number of hydrolysable groups is low.

In some embodiments of method 200, step 202 includes reacting in an inert atmosphere. The inert atmosphere can include inert gases such as argon, nitrogen, or combinations thereof.

In some embodiments of method 200, step 202 includes reacting the halogenated arene and norbornadiene or derivative thereof at an elevated temperature for a period of time. For example, the selected temperature can enhance yield of the ladder-type monomer or reduce the time required for the reaction to be complete. In some embodiments, the temperature of the polymerization is about greater than 90° C., such as about 115° C., about 120° C., about 125° C., about 130° C., about 135° C., or about 140° C. The temperature can be, for example, in a range from about 15-200° C. In some embodiments, the temperature can be in the range of about 25° C. to about 150° C., such as about 50-140° C., about 60-140° C., about 80-140° C., or about 100-130° C. In some embodiments of method 200, the reaction time can be, for example, a period of from about 1 hour to about 72 hours. In some cases, the temperature employed is about 90-135° C. and the duration of the reaction is within the range of about 12-18 hours.

In some embodiments, the conversion of the reactants to the ladder-type monomer can attain yields greater than about 45%. In Some embodiments, conversion of reactants to the ladder-type monomer can be about 50% or greater, about 55% or greater, about 60% or greater, about 65% or greater, about 70% or greater. In some embodiments, conversion of reactants to the ladder-type monomer is substantially quantitative (e.g., near 100%). The determination of yield can be made after the crude reaction product is filtrated and washed.

An intrinsically microporous ladder-type Tröger's base polymer described above can be obtained by in situ formation of a Tröger's base from amino-functionalized monomers. Accordingly, the next step of method 200 is conditional on whether the halogenated arene of step 202 is amine-functionalized. In some embodiments of method 200 the halogenated arene is not aminated, and therefore, the resulting ladder-type monomer requires functionalization according to blocks 204 and 206. A ladder-type monomer made from arenes that are not aminated is also referred to as a first intermediate ladder-type compound. If the halogenated arene is amine-functionalized, method 200 can include forming a Tröger's base by polymerizing the ladder-type diamine monomer directly according to block 208.

As described in block 204, one or more embodiments of method 200 can include nitrating the arene moieties to form an intermediate dinitro compound for subsequent reduction to the diamine. Nitrating includes contacting, under suitable reaction conditions, the ladder-based monomer with an inorganic nitrate in the presence of a carboxylic acid or a carboxylic acid anhydride. The inorganic nitrate can be nitric acid, as such, or formed in situ, either in the presence or absence of another strong acid and in the presence of a solvent. Suitable solvents which can be protonated may be selected from compounds which contain as functional groups either carbonyl or cyano structures (e.g., aliphatic nitriles). Suitable reaction conditions can include dispersing the ladder-type monomer and inorganic nitrate in solvent (e.g., acetonitrile) on ice and adding the carboxylic acid or carboxylic acid anhydride (e.g., trichloroacetic anhydride). The intermediate dinitro compound can be dried over a drying agent (e.g., sodium or magnesium sulfate) and purified using column chromatography, for example. The product can include constitutional isomers including trans- and cis-di(nitroarene) compounds.

In one or more embodiments of the present disclosure, method 200 includes reducing each nitro group of the arene moieties of the intermediate nitro compound to form a ladder-type diamine monomer. Accordingly, within block 206, the method includes providing conditions for reducing at least one of the one of the nitro groups on the arene moieties of the intermediate nitro compound to an amine. Reducing can include catalytic hydrogenation such as palladium-catalyzed hydrazine reduction of the dinitro intermediate of block 204. In some cases, reducing includes contacting the intermediate nitro compound with and/or refluxing in the presence of hydrazine monohydrate and palladium on carbon (Pd/C). The reaction product can include constitutional isomers including trans- and cis-di (aminoarene) compounds. The resulting ladder-type diamine monomer can be precipitated in ice water, filtrated, re-dissolved in solvent, and purified using column chromatography, for example.

After at least two ladder-type diamine monomers as described above have been prepared or obtained, method 200 includes reacting the at least two ladder-type diamine monomers. As shown in block 208, forming an intrinsically microporous ladder-type Tröger's base polymer includes reacting, or polymerizing, trans- and/or cis-di(aminoarene) monomers with a formaldehyde source (e.g., dimethoxymethane, urotropine, dimethylsulfoxide, and paraformaldehyde) under acidic conditions (e.g., HCl, methanesulfonic acid, a Lewis acid such as trifluoroacetic acid (TFA), $AlCl_3$, and $TiCl_4$) in an inert atmosphere at room temperature. The reaction can be a one-pot reaction. In some cases, the Lewis acid can be a Lewis acid catalyst such as TFA. For example, TFA can act as both catalyst and solvent for in situ formation of formaldehyde from dimethoxymethane enables the alkylation and subsequent cyclization of the amino groups to form an intrinsically microporous ladder-type Tröger's base-linked polymer. In some cases, the reaction includes one molar equivalent of the one or more monomers, about 4-7 molar equivalents of the formaldehyde source, and about 30-130 molar equivalents of the acid catalyst. The reaction can proceed until a viscous solution is formed (e.g., too viscous to be stirred with a magnetic stir bar). The reaction can proceed for about 3 hours to about 48 hours. The viscous mixture can be poured into vigorously stirred water or aqueous ammonium hydroxide solution (e.g., about 10%). The resulting solid can be collected by filtration and dried (e.g., in a vacuum oven). The dried product can be washed to remove oligomers. For example, the reaction products can be dissolved in solvent (e.g., chloroform), and precipitated in one or more of methanol and ethanol one or more times. The relative configurations of the polymer defined by the bridging methylene groups in the resulting Tröger's base linkages (i.e., syn and anti) can be arranged randomly along the polymer backbone. The resulting polymer can be characterized by the presence of a repeat unit with the structure of formula (I). In one or more embodiments, the product of method 200 is a polymer with a repeating unit of formula (IV) or (V) above.

Methods of Using an Intrinsically Microporous Ladder-Type Tröger's Base Polymer

Embodiments of the present disclosure describe methods of using an intrinsically microporous ladder-type Tröger's base polymer including a repeat unit of formula (I) as a material for separation of gases, liquids, and molecules dissolved in a solvent (in the form of membranes or solid monolithic structures); porous materials as adsorbents and for catalysis; low dielectric materials; gas storage materials; porous supports; photoresist components; coatings; packaging materials; liquid crystal motifs; plastic additives; and rheological modifiers. A ladder-type Tröger's base polymer membrane having a repeat unit of formula (I) is useful in gas separation processes in air purification, petrochemical, refinery, and natural gas industries. For example, a membrane comprising an intrinsically microporous ladder-type Tröger's base polymer can be used in conventional gas separation systems such as systems to enrich a specific gas content in a gas mixture (e.g., oxygen enrichment, nitrogen enrichment, and the like). In addition, the membranes can be used in hydrogen recovery applications and carbon dioxide removal gas separations.

Figure 3:
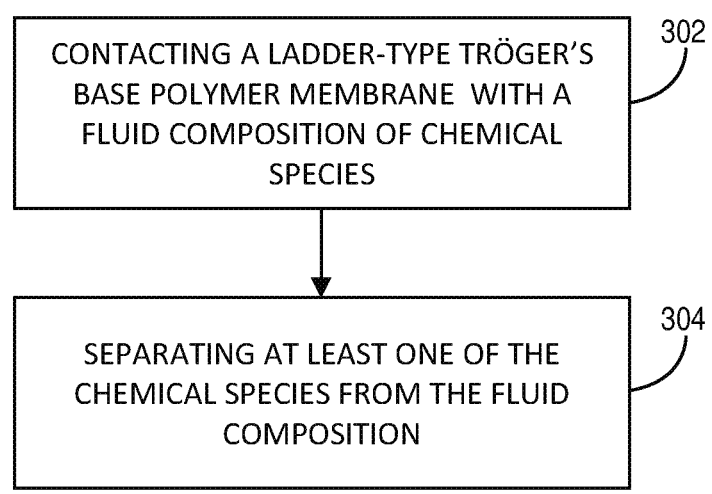
FIG. 3 is a flowchart of a method of separating chemical species, according to one or more embodiments of the present disclosure.

A method of using a membrane comprising an intrinsically microporous ladder-type Tröger's base polymer including a repeat unit of formula (I) is shown in FIG. 3. At block 302, method 300 includes contacting a membrane with a fluid composition comprising a mixture chemical species. The fluid composition can be a fluid in a gas or liquid phase. A gas phase can include both true gases, comprising materials that are gaseous under normal conditions, and also materials that are normally liquid or solid which are maintained in a vapor state for processing. The fluid composition may be a gas mixture, e.g., a mixture of hydrogen, helium, oxygen, nitrogen, carbon monoxide, carbon dioxide, hydrogen sulfide, ammonia, water vapor, a nitrogen oxide, a sulfur oxide, a C1-C8 hydrocarbon, natural gas, an organic vapor, a fluorocarbon, or a refrigerant gas, for example. A membrane may be configured in combination with one or more additional gas separation membranes, including but not limited to, in parallel, series, recycle, and cascade arrangements.

The step of contacting can include providing a fluid composition for gas separation applications. For example, contacting can include providing the fluid composition in the form of a fluid stream to one or more surfaces of the membrane. Accordingly, step 302 can include contacting a first surface of the membrane with the fluid stream. The fluid stream can include air, flue gas, digester gas, fermentation gas, sewage gas, natural gas, coal gas, synthesis gas, or combinations thereof. In some cases, the fluid stream includes hydrogen, carbon dioxide, carbon monoxide, sulfur dioxide, helium, hydrogen sulfide, nitrogen, oxygen, argon, hydrogen sulfide, nitronic oxide, nitrous oxide, nitric oxide, ammonia, a hydrocarbon of one to five carbon atoms, hydrogen chloride, or a combination thereof. For example, the fluid stream can include air, air and methane, air and carbon dioxide, air and carbon monoxide, methane and carbon dioxide, methane and H₂S, methane and carbon monoxide, hydrogen and carbon monoxide, or combination thereof.

At step 304, the method includes separating at least one chemical species from the fluid composition. For example, a portion of the fluid composition comprising at least one chemical species passes through the membrane and exits the membrane as a permeate, whereas another portion of the fluid composition does not pass through the membrane. Separating can provide preferential depletion or concentration of one or more of the chemical species in the fluid composition and provide a product having a different proportion of the one or more desired components to the at least one other component than that proportion in the mixture. The permeate can be oxygen-enriched or a nitrogen-enriched, for example, relative to the fluid composition. The portion of the fluid composition that does not permeate the membrane can be nitrogen-enriched, oxygen-enriched, carbon dioxide-enriched, nitrogen-depleted, oxygen-depleted, or carbon dioxide-depleted relative to the fluid composition. For example, if the fluid composition included hydrogen gas, the permeate can be hydrogen-enriched, and the portion that does not permeate can be hydrogen depleted relative to the fluid composition. In some cases, the method can be used to generate hydrogen sulfide-depleted methane, hydrogen-enriched syngas, or a combination thereof. The method can be used to an enriched nitrogen stream for inerting of flammable fluids, perishable foodstuffs, and metal treating processes; an enriched oxygen stream for medical or industrial uses, fermentation processes, enhanced combustion processes; or an enriched hydrogen stream for hydrocracking or hydrogenating aromatics, for example.

In addition, a membrane comprising an intrinsically microporous ladder-type Tröger's base polymer including a repeat unit of formula (I) can be useful for separating gases and/or vapors from mixtures of liquids or mixtures of liquids and gases using the membrane separation processes of membrane stripping or membrane distillation. For example, a chemical species permeating through or across the membrane can be removed as a gas or a vapor or can be condensed and removed as a liquid.

The operating temperature of the separating may vary depending upon the temperature of the fluid composition (e.g., fluid stream) and upon ambient temperature conditions. In some cases, the effective operating temperature of the membranes of the present invention can be within the range of about −50° to about 350° C.

Although not shown in FIG. 3, in some cases, method 300 can include an initial step of preparing the membrane as described above (e.g., casting or spinning). Preparing can include providing conditions that enable the prepared membrane to withstand the conditions it may be subjected to during the separation operation (e.g., providing sufficient composition to cast a membrane of the desired thickness, and avoiding conditions that may accelerate physical aging). Preparing can include characterizing the the gas transport properties of the membrane to ensure adequately selective separation of the one or more desired chemical species, and/or a high permeation rate.

A first aspect of the present disclosure will now be described with reference to the following embodiments, of which:

A first embodiment is a composition comprising an intrinsically microporous ladder-type Tröger's base polymer comprising a repeat unit represented by formula (I):

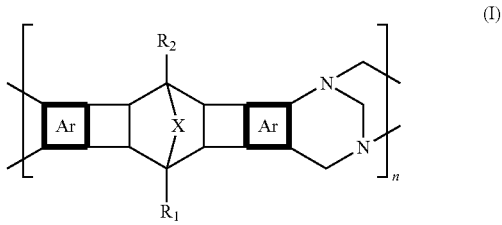

wherein each Ar is independently selected from an unsubstituted or substituted aryl group; X is a carbon or heteroatom bridging moiety selected from —[O]—, —[S]—, —[B(O)R$^a$]—, —[NR$^a$]—, —[P(O)R$^a$]—, —[(PO)(O)R$^a$]—, —[CO]—, —[—CR$^a$R$^b$]—, —[C(O)R$^a$(O)R$^b$]—, or —[Si(O)R$^a$(O)R$^b$]—, and R$^a$ and R$^b$ are independently selected from the group consisting of hydrogen, alkyl groups, aryl groups, and heterocyclic groups; R$_1$ and R$_2$ are independently selected from the group consisting of hydrogen, unsubstituted and substituted, linear or branched alkyl groups, substituted and unsubstituted alkoxy groups, substituted and unsubstituted aryl groups, heterocyclic groups, halogen groups, —CHO, groups having an —O— moiety, groups having an —O(CO)— moiety, groups having an —O(CO)O— moiety, groups having an —O(CO)N< moiety, groups having a —S— moiety, groups having a —B< moiety, —NO₂, groups having a —N< moiety, groups having a —P< moiety, groups having a —(PO)< moiety, groups having a —(CO)— moiety, groups having a —(CO)O— moiety, groups having a —(CO)N< moiety and groups having a —Si═moiety; and n is an integer greater than 1.

A second embodiment is the composition of the first embodiment, in which the intrinsically microporous ladder-type Tröger's base polymer has a BET surface area greater than about 600 m² g$^{-1}$.

A third embodiment is the composition of the first embodiment or the second embodiment in which X is a carbon, R$_1$ and R$_2$ are hydrogen, and each Ar is independently selected from the group consisting of:

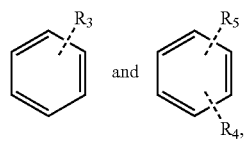

wherein R$_3$, R$_4$, and R$_5$ are each independently selected from the group consisting of linear or branched unsubstituted or substituted alkyl groups, unsubstituted or substituted alkoxy groups, unsubstituted or substituted unsaturated aliphatic groups, unsubstituted or substituted cycloalkyl groups, unsubstituted or substituted aryl groups, unsubstituted or substituted heterocyclic groups, —CHO, groups having a —O— moiety, groups having a —O(CO)— moiety, groups having a —O(CO)O— moiety), groups having a —O(CO)N< moiety, groups having a —S— moiety, groups having a —B< moiety, —NO₂, groups having a —N< moiety, groups having a —P< moiety, groups having a —PO< moiety, groups having a —(CO— moiety, groups having a —(CO)O— moiety, groups having a —(CO)N< moiety, and groups having a —Si≡ moiety.

A fourth embodiment is the composition of the first, second, or third embodiment, in which the repeat unit has the following structure:

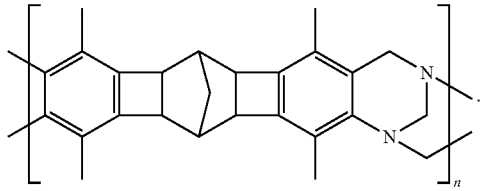

A fifth embodiment is the composition of the first, second, third or fourth embodiment in which wherein the repeat unit has the following structure:

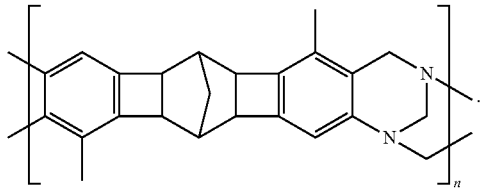

A seventh embodiment is the composition of the first, second, third, fourth, fifth or sixth embodiment in which the composition is configured as a flat sheet membrane, a rolled flat sheet membrane, a supported membrane, a cylinder, a tube, a capillary, a hollow fiber, or a powder.

An eighth embodiment is the composition of the seventh embodiment in which the composition has a thickness of about 1 to 30 μm.

A ninth embodiment is the composition of the first, second, third, fourth, fifth, sixth, seventh, or eighth embodiment in which the intrinsically microporous ladder-type Tröger's base polymer has a bimodal pore size distribution comprising ultramicropores.

A second aspect of the present disclosure with be described with reference to the following embodiments, in which, A first embodiment of the second aspect is method of synthesizing an intrinsically microporous ladder-type Tröger's base polymer comprising:
(a) forming a ladder-type diamine monomer by catalytic arene-norbornene annulation (CANAL) polymerization of a halogenated arylamine and norbornadiene or a derivative thereof, wherein the molar ratio of the halogenated arylamine to norbornadiene or the derivative thereof is 2:1, or
(a1) forming a first intermediate ladder-type compound by CANAL polymerization of a halogenated arene and norbornadiene or a derivative thereof, wherein the ratio of the halogenated arene to norbornadiene or the derivative thereof is 2:1; and
(a2) nitrating the first intermediate ladder-type compound to form an intermediate ladder-type dinitro compound; and
(a3) reducing the two nitro groups of the intermediate ladder-type dinitro compound to form a ladder-type diamine monomer; and (b) reacting at least two of the ladder-type diamine monomers to form the intrinsically microporous ladder-type Tröger's base polymer comprising a repeat unit represented by formula (I):

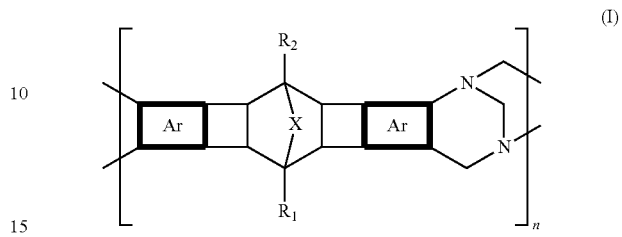

wherein each Ar is independently selected from an unsubstituted or substituted aryl group; X is a carbon or heteroatom bridging moiety selected from —[O]—, —[S]—, —[B(O)R$^a$]—, —[NR$^a$]—, —[P(O)R$^a$]—, —[(PO)(O)R$^a$]—, —[CO]—, —[—CR$^a$—R$^b$]—, —[C(O)R$^a$(O)R$^b$]—, or —[Si(O)R$^a$(O)R$^b$]—, and R$^a$ and R$^b$ are independently selected from the group consisting of hydrogen, alkyl groups, aryl groups, and heterocyclic groups; $R_1$ and $R_2$ are independently selected from the group consisting of hydrogen, unsubstituted and substituted, linear or branched alkyl groups, substituted and unsubstituted alkoxy groups, substituted and unsubstituted aryl groups, heterocyclic groups, halogen groups, —CHO, groups having an —O— moiety, groups having an —O(CO)— moiety, groups having an —O(CO)O— moiety, groups having an —O(CO)N< moiety, groups having a —S— moiety, groups having a —B< moiety, —NO$_2$, groups having a —N< moiety, groups having a —P< moiety, groups having a —(PO)< moiety, groups having a —(CO)— moiety, groups having a —(CO)O— moiety, groups having a —(CO)N< moiety and groups having a —Si≡ moiety; and n is an integer greater than 1.

A second embodiment of the second aspect is the method of the first embodiment including performing step (a), wherein the halogenated arylamine has the following structure:

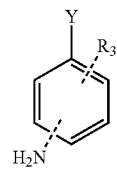

wherein Y can be a chloro, bromo, or iodo group, $R_3$ is selected from the group consisting of linear or branched unsubstituted or substituted alkyl groups, unsubstituted or substituted unsaturated aliphatic groups, unsubstituted or substituted cycloalkyl groups, unsubstituted or substituted aryl groups, unsubstituted or substituted heterocyclic groups, and unsubstituted or substituted alkoxy groups, —CHO, groups having a —O— moiety, groups having a —O(CO)— moiety, groups having a —O(CO)O— moiety), groups having a —O(CO)N< moiety, groups having a —S— moiety, groups having a —B< moiety, —NO$_2$, groups having a —N< moiety, groups having a —P< moiety, groups having a —PO< moiety, groups having a —(CO)— moiety, groups having a —(CO)O— moiety, groups having a —(CO)N< moiety, and groups having a —Si≡ moiety.

A third embodiment of the second aspect is the method of the first embodiment including performing steps (a1)-(a3), wherein the halogenated arene has the following structure:

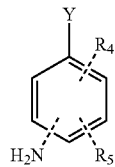

wherein Y can be a chloro, bromo, or iodo group, $R_4$ and $R_5$ are independently selected from the group consisting of linear or branched unsubstituted or substituted alkyl groups, unsubstituted or substituted unsaturated aliphatic groups, unsubstituted or substituted cycloalkyl groups, unsubstituted or substituted aryl groups, unsubstituted or substituted heterocyclic groups, and linear or branched unsubstituted or substituted alkoxy groups, —CHO, groups having a —O— moiety, groups having a —O(CO)— moiety, groups having a —O(CO)O— moiety), groups having a —O(CO)N< moiety, groups having a —S— moiety, groups having a —B< moiety, —NO$_2$, groups having a —N< moiety, groups having a —P< moiety, groups having a —PO< moiety, groups having a —(CO— moiety, groups having a —(CO)O— moiety, groups having a —(CO)N< moiety, and groups having a —Si≡ moiety.

A fourth embodiment of the second aspect is the method of the first or third embodiment in which nitrating includes contacting the first intermediate compound with an inorganic nitrate and one of a carboxylic acid or carboxylic acid anhydride.

A fifth embodiment of the second aspect is the method of the first, third or fourth embodiment in which reducing includes catalytic hydrogenation.

A sixth embodiment of the second aspect is the method of the fifth embodiment in which catalytic hydrogenation comprises refluxing the intermediate dinitro compound in the presence of hydrazine monohydrate and palladium on carbon.

A seventh embodiment of the second aspect is the method of the first, second, third, fourth, fifth or six embodiment in which step (b) comprises reacting the ladder-type diamine monomers with a formaldehyde source and a Lewis acid catalyst.

A third aspect of the present disclosure will be described with reference to the following embodiments:

A first embodiment of the third aspect is a method of separating a chemical species in a fluid composition comprising:

(a) contacting a membrane comprising an intrinsically microporous ladder-type Tröger's base polymer a with a fluid composition comprising at least two chemical species; and (b) separating a first chemical species from the fluid composition;

wherein the intrinsically microporous ladder-type Tröger's base polymer comprises a repeat unit represented by formula (I):

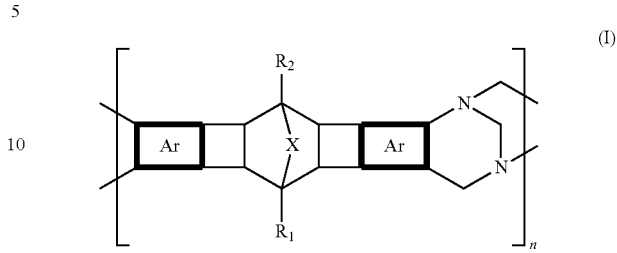

wherein each Ar is independently selected from an unsubstituted or substituted aryl group; X is a carbon or heteroatom bridging moiety selected from —[O]—, —[S]—, —[B(O)R$^a$]—, —[NR$^a$]—, —[P(O)R$^a$]—, —[(PO)(O)R$^a$]—, —[CO]—, —[—CR$^a$—R$^b$]—, —[C(O)R$^a$(O)R$^b$]—, or —[Si(O)R$^a$(O)R$^b$]—, and R$^a$ and R$^b$ are independently selected from the group consisting of hydrogen, alkyl groups, aryl groups, and heterocyclic groups; $R_1$ and $R_2$ are independently selected from the group consisting of hydrogen, unsubstituted and substituted, linear or branched alkyl groups, substituted and unsubstituted alkoxy groups, substituted and unsubstituted aryl groups, heterocyclic groups, halogen groups, —CHO, groups having an —O— moiety, groups having an —O(CO)— moiety, groups having an —O(CO)O— moiety, groups having an —O(CO)N< moiety, groups having a —S— moiety, groups having a —B< moiety, —NO$_2$, groups having a —N< moiety, groups having a —P< moiety, groups having a —(PO)< moiety, groups having a —(CO)— moiety, groups having a —(CO)O— moiety, groups having a —(CO)N< moiety and groups having a —Si≡ moiety; and n is an integer greater than 1.

A second embodiment of the third aspect is the method of the first embodiment in which the fluid composition is selected from the group consisting of air, natural gas, flue gas, ammonia synthesis purge streams, hydrocarbon processing gas, steam reforming gas, gasification process gas, off-gases from refinery or petrochemical plants, and a combination thereof.

A third embodiment of the third aspect is the method of the first or second embodiment in which the fluid composition comprises a gaseous chemical species selected from the group consisting of $H_2$, $O_2$, $N_2$, Ar and $CO_2$.

A fourth embodiment of the third aspect is the method of the first, second, or third embodiment in which the membrane is permeable to one or more of $H_2$, $O_2$, $N_2$, Ar and $CO_2$.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

Example 1

Arene-Norbornene-Tröger's Base-Derived Ladder Polymers

Membrane-based gas separation processes are emerging in a variety of large-scale industrial applications, such as hydrogen recovery from petrochemical process streams, onsite nitrogen generation ($O_2/N_2$) and acid gas removal from natural gas ($CO_2$, $H_2S$), etc. To achieve technically and economically viable processes ideal membranes require high permeability and selectivity. One polymer class that has shown potential as advanced gas separation membrane material is based on polymers of intrinsic microporosity (PIM). These ladder polymers contain certain types of sterically hindered contortion centers, such as spirobisindane, spirobifluorene, ethanoanthracene, triptycene and Tröger's base. PIMs are extremely rigid, solution processible polymers with large BET surface area. To date, synthesis of ladder-type PIMs is limited by the availability of only a few building blocks with sterically hindered contortion sites. Therefore, design of novel building blocks is highly desirable for development of optimized ladder-type PIMs. The present disclosure describes Arene-Norbornene-Tröger's base-derived PIMs (ANTB-PIM) and methods of preparing ANTB-PIMs by linking an arene-norbornene building block to a Tröger's base.

The synthetic routes according to one or more embodiments of the present disclosure are shown in Scheme 1 and Scheme 2. In Scheme 1, amine-functionalized bromobenzene is reacted via catalytic arene-norbornene annulation (CANAL) to provide diamines to form ANTB-PIM.

polymers, where X and Y can be independently selected from hydrogen, or one of the groups described above for $R_3$, $R_4$, and $R_5$ above. For example, X and Y can be independently a hydrogen, a linear or branched lower alkyl group ($C_nH_{2n+1}$) (e.g., methyl, ethyl, n-propyl, iso-propyl, n-butyl, sec-butyl, T-butyl, n-pentyl, iso-pentyl, and sec-pentyl), a cycloalkyl group ($C_nH_{2n-1}$), an alkoxy group (e.g., methoxy, ethoxy, propoxy, isopropoxy, butoxy, sec-butoxy, isobutoxy, tert-butoxy, pentoxy, hexoxy, and the like), a cycloalkoxy group, and n is an integer greater than 1 (e.g., greater than 5). Although bromine is shown, the halogen can be selected from fluorine, chlorine, bromine, or iodine.

In Scheme 2, exemplary diamines for ANTB-PIMs are obtained by nitration and reduction of the Arene-Norbornene-based building block.

SCHEME 2. General synthetic route 2 for the arene-norbornene Tröger's base ladder polymers

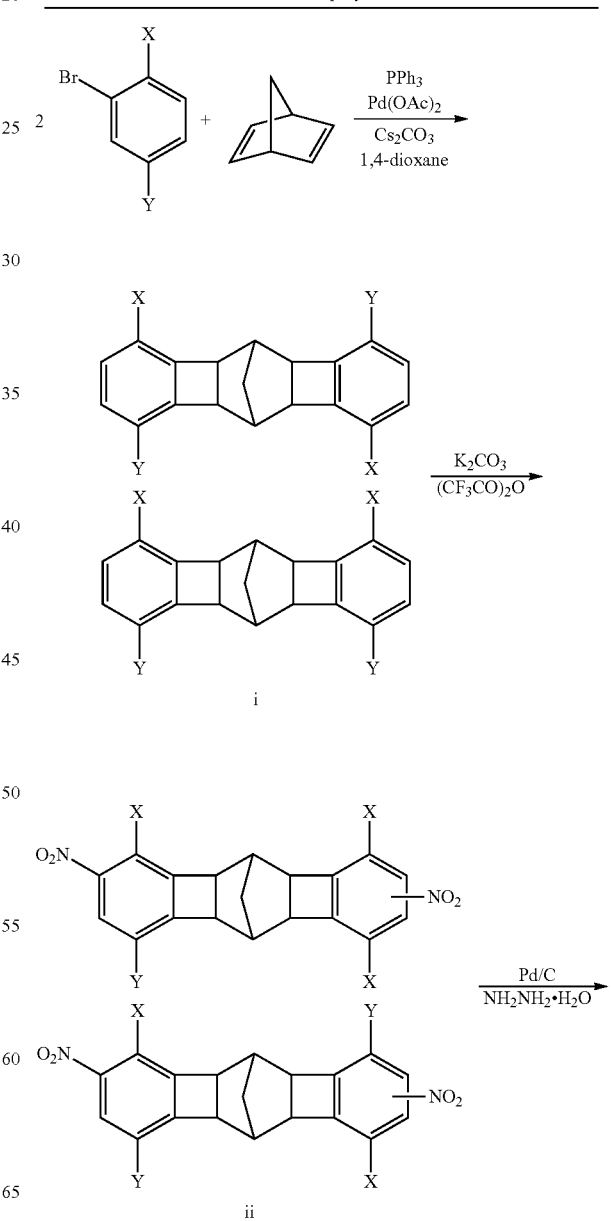

SCHEME 1. General synthetic route 1 for the arene-norbornene Tröger's base ladder

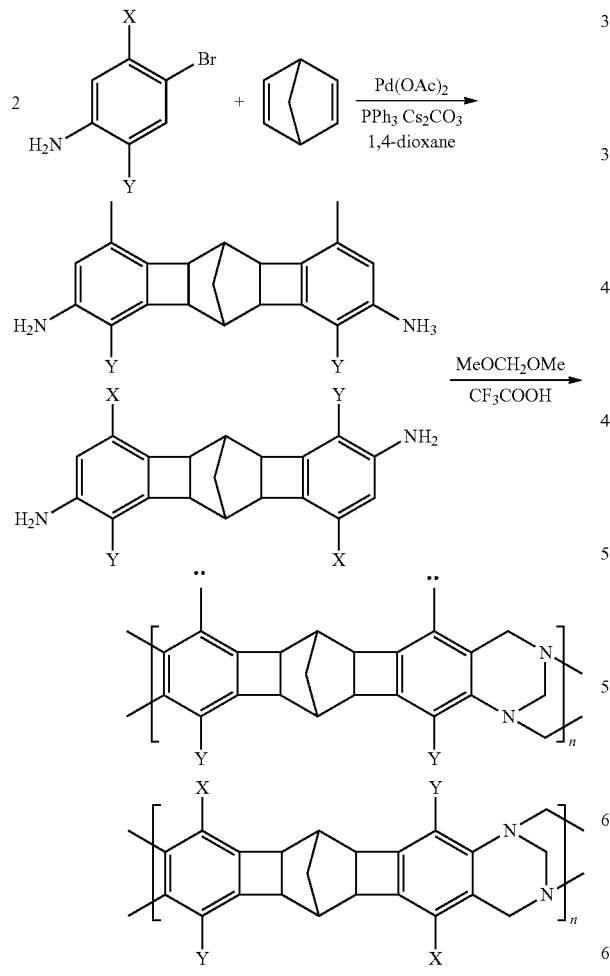

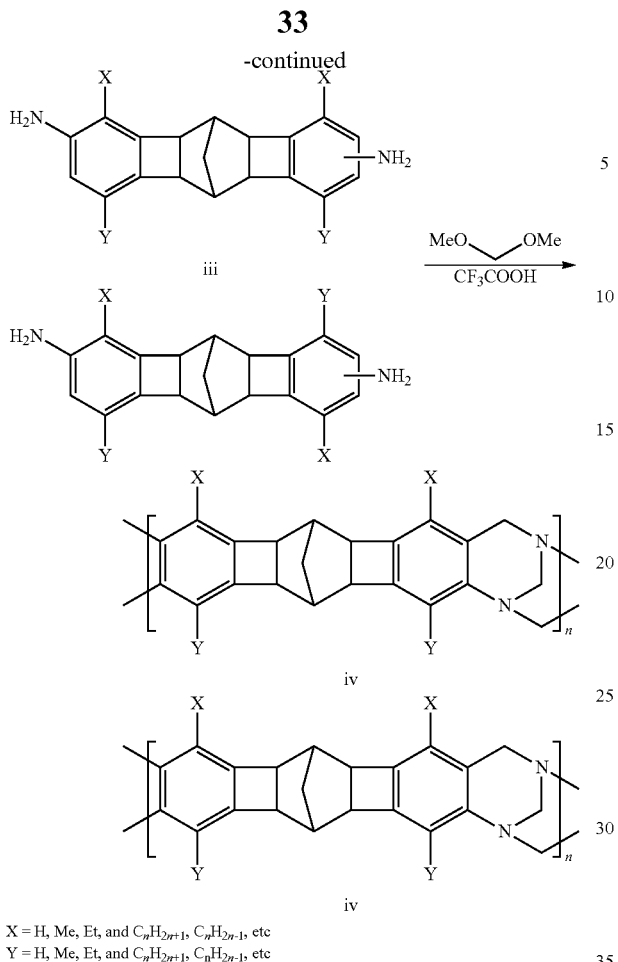

X = H, Me, Et, and $C_nH_{2n+1}$, $C_nH_{2n-1}$, etc
Y = H, Me, Et, and $C_nH_{2n+1}$, $C_nH_{2n-1}$, etc where X and Y can be independently selected from hydrogen, or one of the groups described above for $R_3$, $R_4$, and $R_5$ above. For example, X and Y can be independently a hydrogen, a linear or branched lower alkyl group ($C_nH_{2n+1}$) (e.g., methyl, ethyl, n-propyl, iso-propyl, n-butyl, sec-butyl, t-butyl, n-pentyl, iso-pentyl, and sec-pentyl), a cycloalkyl group ($C_nH_{2n-1}$), an alkoxy group (e.g., methoxy, ethoxy, propoxy, isopropoxy, butoxy, sec-butoxy, isobutoxy, tert-butoxy, pentoxy, hexoxy, and the like), a cycloalkoxy group, and n is an integer greater than 1 (e.g., greater than 5). Although bromine is shown, the halogen can be selected from fluorine, chlorine, bromine, or iodine.

Example 2

Development of Arene-Norbornene-Tröger's Base Ladder Polymers as Highly Efficient Gas Separation Membranes The following examples describe the synthesis of two novel organosoluble intrinsically microporous ladder-type Tröger's base polymers (SP-TB-1 and SP-TB-2) using dibenzocyclobutanorbornane and Tröger's base as building blocks. SP-TB-1 and SP-TB-2 exhibited very high BET surface areas of 881 and 987 m$^2$ g$^{-1}$, respectively. Low temperature N$_2$ sorption-derived pore size distribution reveals a large fraction of ultramicropores (<7 Å). Isotropic films based on the SB-TB ladder polymers exhibited strong molecular sieving properties due to their highly contorted and rigid W-shaped dibenzocyclobutanorbornane and V-shaped Tröger's base building blocks. The overall performance of the SP-TB ladder polymers is located between the reported 2008 and 2015 permeability/selectivity trade-off curves for H$_2$/N$_2$ and O$_2$/N$_2$ separations. 300-day aged SP-TB-1 exhibited notable H$_2$ and O$_2$ permeability of 1163 and 204 barrer with H$_2$/N$_2$ and O$_2$/N$_2$ selectivity of 29.8 and 5.2, respectively. The tetramethyl-substituted ladder polymer (SP-TB-2) exhibited higher permeability coupled with lower selectivities than the dimethyl-based SP-TB-1 polymer due to a more twisted structure leading to more inefficient chain packing and higher free volume.

These examples detail synthesis of ladder PIM obtained by combining W-shaped arene-norbornene and V-shaped Tröger's base building blocks in a single polymer repeat unit. The synthetic procedures for two related ladder PIMs, SP-TB-1 and SP-TB-2, are shown in Scheme 3. SP-TB-1 and SP-TB-2 were synthesized and their physical and gas transport properties were fully characterized.

SCHEME 3. Synthetic Routes of the Arene-Norbornene and Tröger's Base-Based Ladder-Type Polymers (SP-TB-1 and SP-TB-2).

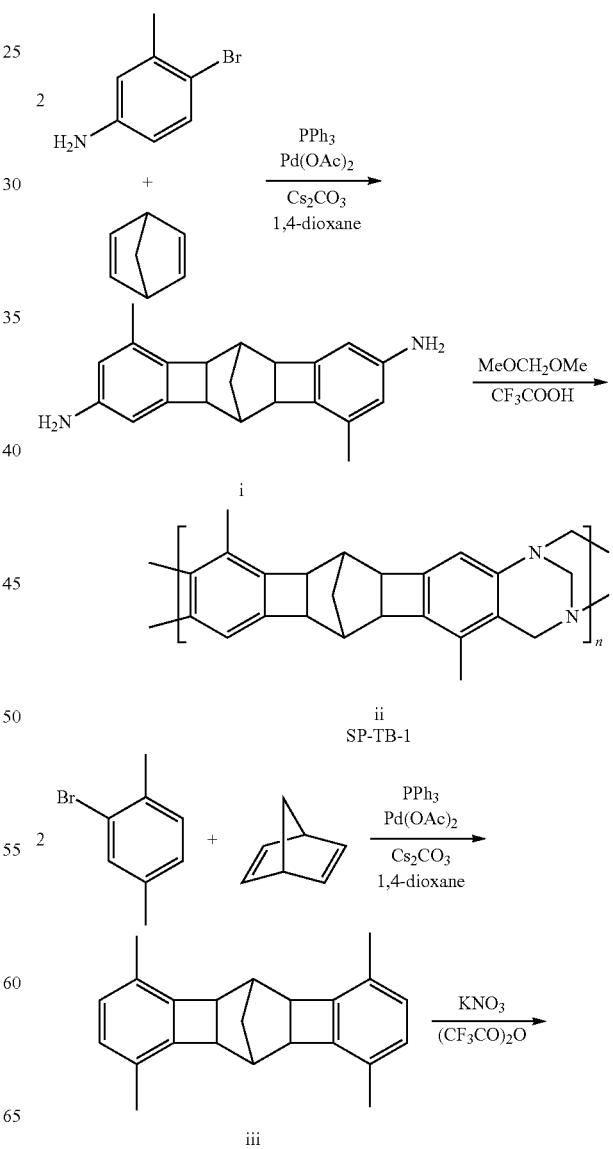

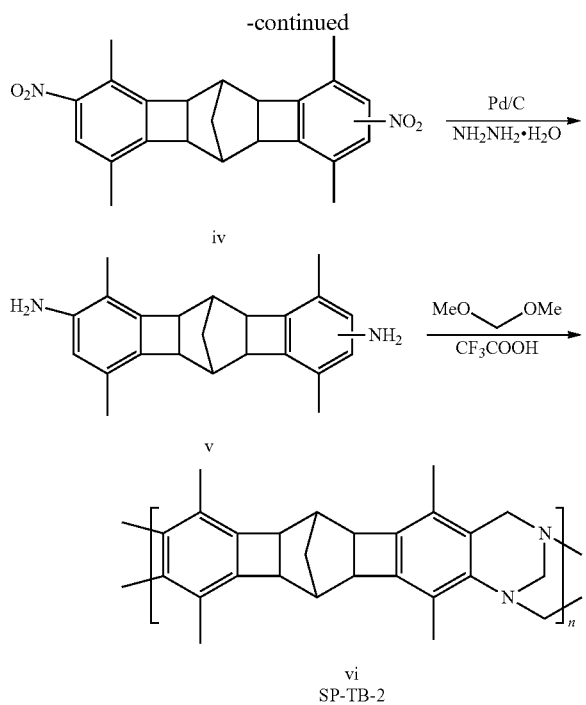

vi
SP-TB-2

Experimental Section

Materials

4-Bromo-3-methylaniline, 2-bromo-1,4-dimethylbenzene, palladium(II) acetate (Pd(OAc)$_2$), cesium carbonate (Cs$_2$CO$_3$), triphenylphosphine, CELITE® (Filter Aid, Diatomaceous earth, flux-calcined), silica gel, palladium on carbon, potassium nitrate (KNO$_3$), anhydrous 1,4-dioxane, (1s,4s)-bicyclo[2.2.1] hepta-2,5-diene (norbornadiene, containing 250 ppm BTH), dichloromethane, trifluoroacetic acid (CF$_3$COOH), CH$_3$CN, trifluoroacetic anhydride, hydrazine monohydrate (50%), methoxymethane, ammonium hydroxide solution (33%) and ethanol were obtained from Sigma-Aldrich and used as received.

Characterization and Methods $^1$H NMR and $^{13}$C NMR spectra of the monomers and polymers were recorded with an AVANCE™-III spectrometer (Bruker BioSpin, Billerica, Mass.) at a frequency of 400 or 500 MHz in deuterated chloroform or dimethylsulfone with tetramethylsilane as an internal standard. High-resolution mass spectroscopy (HRMS) of the monomers was performed with a ThermoFisher Scientific™ LC/MS system with LTQ Orbitrap™ Velos detectors. Thermal gravimetric analysis (TGA) was carried out with a TGA Q5000 (TA Instruments, New Castle, Del.). Differential scanning calorimetric analysis (DSC) and melting point of the polymers and intermediates were recorded on a DSC Q2000 (TA Instruments, New Castle, Del.). Density was obtained using a METTLER-TOLEDO® balance equipped with a density measurement kit based on Archimedes' principle using iso-octane as the reference liquid. The BET surface area of the polymers was measured by N$_2$ adsorption at −196° C. (ASAP 2020, V4.02, MICROMETIRICS®, Norcross, Ga.). The pore size distributions of the polymers were derived from N$_2$ adsorption using the NLDFT method using N$_2$ at 77 K. Wide-angle X-ray scattering of the membrane samples were conducted on a diffractometer (D8 ADVANCE, Bruker, Billerica, Mass.) using a scanning rate of 0.5° min$^{-1}$ from 6 to 50°. Dynamic mechanical stress-strain curves of the polymers were measured using a dynamic mechanical analyzer (Q800 DMA, TA Instruments, New Castle, Del.). The samples were kept at 25° C. and ramped at 3 N min$^{-1}$ to 18 N.

Synthesis of 4,9-dimethyl-4b,5,5a,9b,10,10a-hexahydro-5,10-methanobenzo[3,4] cyclobuta [1,2-b] biphenylene-2,7-diamine (i or SP-1-diamine)

4-Bromo-3-methylaniline (163 mg, 1.00 mmol), Pd(OAc)$_2$ (11.2 mg, 0.05 mmol) and Cs$_2$CO$_3$ (390 mg, 1.2 mmol) were added to a 30 mL glass pressure tube and flashed with N$_2$ for 5 min. Anhydrous 1,4-dioxane (1 mL) and norbornadiene (46 mg, 0.5 mmol, d=0.906 g/mL) were added in sequence. The system was sealed and heated to 130° C. for 12 h and then cooled to room temperature. The crude product was filtrated through a CELITE pad and washed three times with dichloromethane. The organic phase was removed using a rota-evaporator, and the residual was re-dissolved in dichloromethane followed by loading onto a column. A light yellow solid (with both isomers) was obtained by column chromatography and the pure product was obtained as a white solid (105 mg, yield: 70%). The pure symmetric isomer was obtained by crystallization with methanol for three times (yield: 30%). TLC, eluent: hexane/ethyl acetate=1/1, $R_f$=0.35; mp: 227.2° C.; $^1$H NMR (500 MHz, DMSO-d$_6$): δ 6.14 (s, 2H), 6.04 (s, 2H), 4.68 (s, 4H), 2.97 (t, 4H, J=1.56 Hz, 1.56 Hz), 2.12 (m, 2H), 1.97 (s, 6H), 0.63 (s, 2H); $^{13}$C NMR (125 MHz, DMSO-d$_6$): δ 149.2, 146.1, 132.0, 131.9, 114.5, 105.8, 48.0, 47.3, 36.7, 26.4, 17.0; FT-IR (wavenumber, cm$^{-1}$):3398, 3330, 3205 (m, asymmetric N—H vibration), 2939 (s, asymmetric C—H vibration), 1618, 1600 (s, Aromatic C=C vibration), 1480, 1456, 1350 (symmetric C—H rotation), 1208, 1173 (s, asymmetric C—N vibration), 850 (s, Rotation of =C—H); HRMS for [C$_{21}$H$_{23}$N$_2$]$^+$: Calcd. for 303.1856; Found. 303.1850. Elemental analysis ("Anal.") for C$_{21}$H$_{22}$N$_2$; C, 83.40; H, 7.33; N, 9.26; Found: C, 83.92; H, 7.29; N, 9.23.

Synthesis of SP-TB-1

Figure 4:
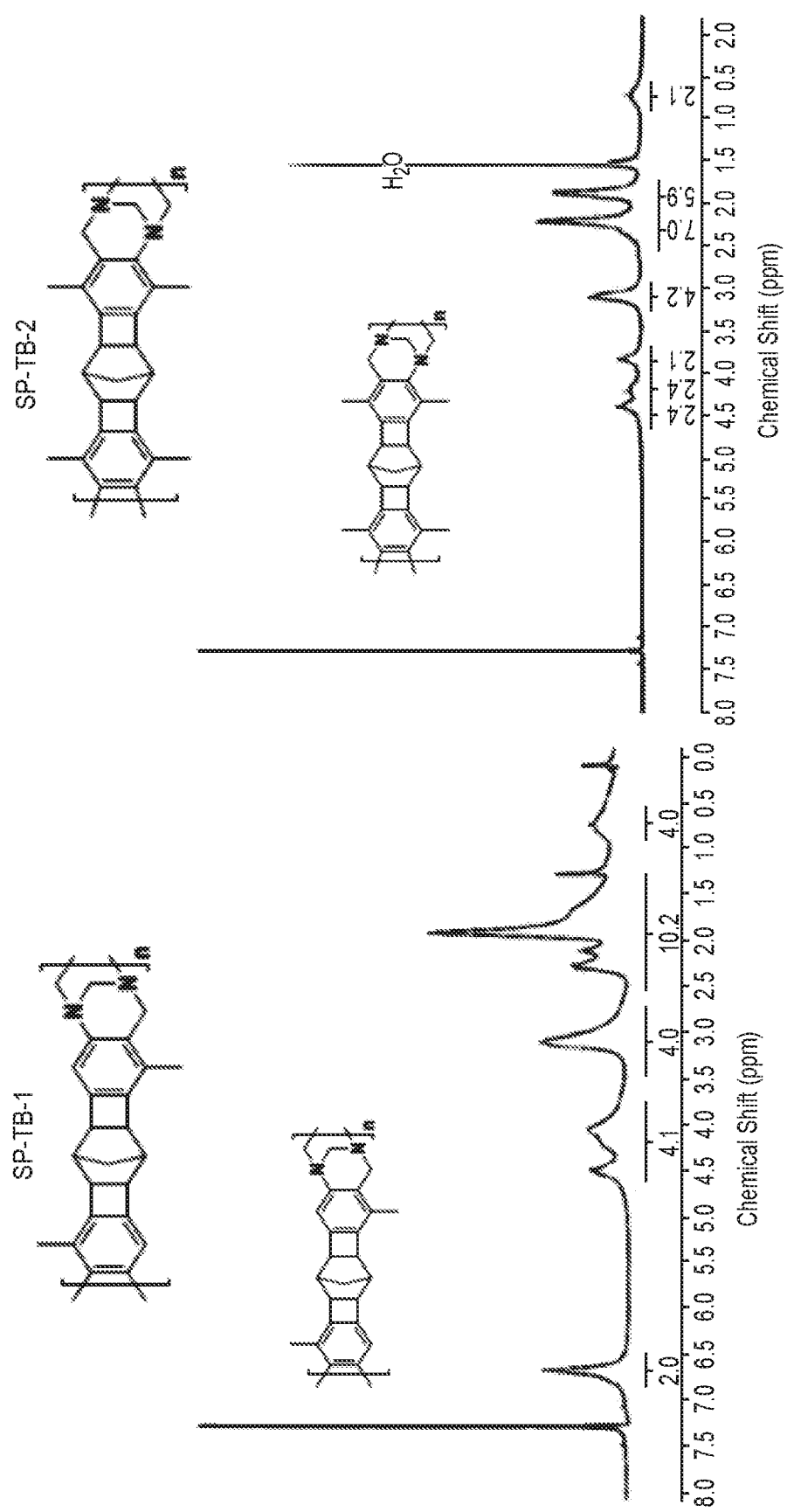
FIG. 4 shows the chemical structure of SP-TB-1 and SP-TB-2, according to one or more embodiments of the present disclosure, as well as their NMR spectra.
Figure 5A:
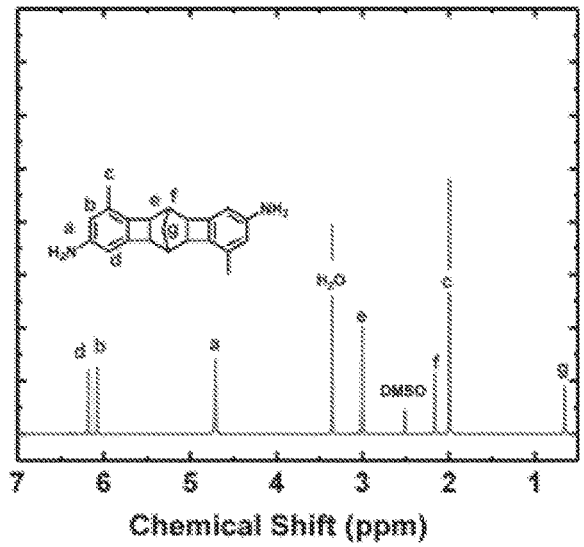
FIG. 5A-D show the $^1$H NMR of the (A) SP-1-diamine (i); (B) SP-TB-1; (C) SP-2-diamine (v); and (D) SP-TB-2, according to one or more embodiments of the present disclosure.
Figure 5B:
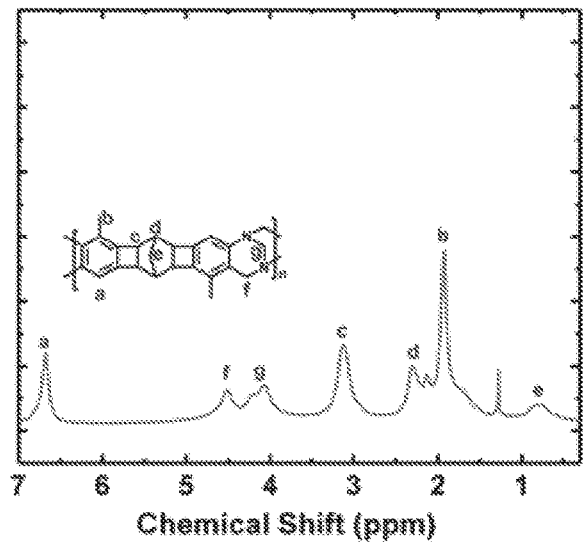
Figure 5C:
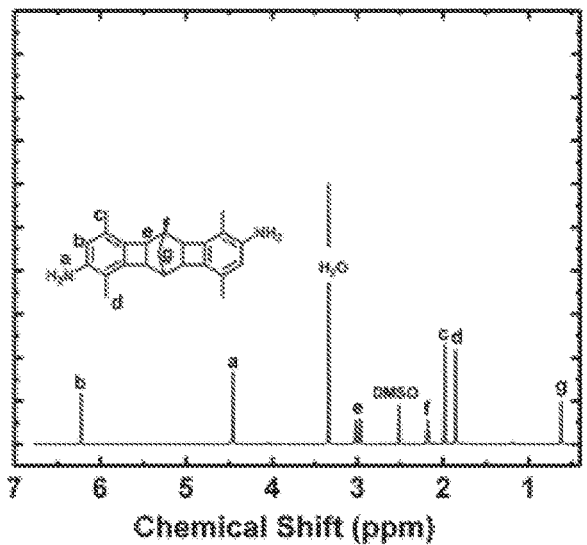
Figure 5D:
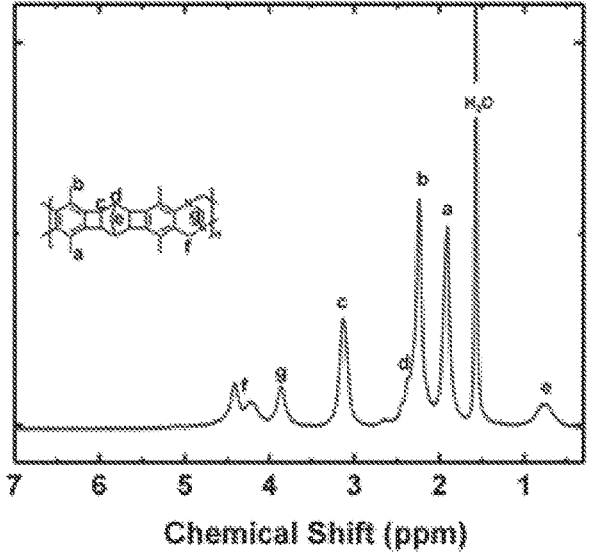

The diamine monomer i (453 mg, 1.50 mmol), dimethoxymethane (570 mg, 7.5 mmol) were added to a 20 mL vial and cooled in an ice-bath. After flushing with N$_2$ for 5 min, CF$_3$COOH (3.72 mL) was added dropwise. The solution was further stirred in the cold bath for 0.5 h and then at room temperature for 3 h. A viscous solution was formed and poured into a 10% ammonium hydroxide solution (100 mL). Polymer filaments were precipitated and continuously stirred for another 2 h before filtration. The solids were dried in a vacuum oven at 120° C. for 2 h. After dissolving in chloroform and re-precipitation in methanol twice, an off-white filament (450 mg, yield: 81.5%) was obtained after drying in a vacuum oven. NMR spectra is shown in FIG. 4. $^1$H NMR (500 MHz, CDCl$_3$): δ 6.68 (s, 2H), 4.06-4.50 (m, 4H), 3.10 (s, 4H), 1.92-2.30 (m, 10H), 0.75 (s, 2H); FT-IR (Wavenumber, cm$^{-1}$): 2939 (s, asymmetric C—H vibration), 1579, 1454 (s, aromatic C=C vibration), 1350 (symmetric C—H rotation), 1200, 1156, 1104 (s, asymmetric C—N vibration); Tas %=440° C.; $S_{BET}$=881 m$^2$ g$^{-1}$; Anal. Calculated (Calcd.) for: C, 86.15; H, 6.12; N, 7.73; Found: C, 86.11; H, 6.37; N, 8.24.

Synthesis of 1,4,6,9-tetramethyl-4b,5,5a,9b,10,10a-hexahydro-5,10-methanobenzo[3,4] cyclobuta[1,2-b]biphenylene (iii)

2-Bromo-1,4-dimethylbenzene (24.0 g, 130 mmol), (1s, 4s)-bicyclo[2.2.1]hepta-2,5-diene (5.89 g, 63.7 mmol), Pd(OAc)$_2$ (675 mg, 3.0 mmol), PPh$_3$ (1.572 g, 6.00 mmol), Cs$_2$CO$_3$ (45.0 g, 137.5 mmol) and 1,4-dioxane (60 mL) were added to a 250 mL pressure flask under N$_2$ atmosphere for 5 min. The reaction system was heated to 90° C. for 0.5 h and then the temperature was increased to 135° C. for 18 h. Thereafter, the solution was cooled to room temperature, filtrated through a CELITE pad and washed three times with dichloromethane. The organic phase was removed using rota-evaporation and the solid was re-dissolved in dichloromethane and then loaded onto a column packed with silica gel. The product was obtained as off-white needle crystals (9.00 g, yield: 47%) after column chromatography. TLC: dichloromethane/petroleum ether=1/5; R$_f$=0.6; $^1$H NMR (500 MHz, CDCl$_3$): δ 6.93 (s, 4H), 3.26 (s, 4H), 2.41 (s, 2H), 2.21 (s, 12H), 0.79 (s, 2H); $^{13}$C NMR (125 MHz, CDCl$_3$): δ 144.3, 129.1, 128.4, 47.9, 35.4, 26.4, 16.3.

Synthesis of 1,4,6,9-tetramethyl-2,7-dinitro-4b,5,5a, 9b,10,10a-hexahydro-5,10-methano benzo[3,4]cyclobuta[1,2-b]biphenylene and 1,4,6,9-tetramethyl-2,6-dinitro-4b,5,5a,9b, 10, 10a-hexahydro-5,10-methanobenzo[3,4]cyclobuta[1,2-b]biphenyl-ene (iv)

Intermediate iii (4.87 g, 16.2 mmol) and KNO$_3$ (3.361 g, 33.2 mmol) were dispersed in acetonitrile (200 mL), which was cooled in an ice-bath and stirred for 15 min. Trifluoroacetic anhydride (20 mL) was added dropwise. After the addition, the system was stirred at room temperature for 0.5 h and poured into 1L water. A viscosity liquid was formed and re-dissolved in dichloromethane. The organic phase was washed with KOH (aq), water and thereafter dried with magnesium sulfate. Finally, the organic phase was removed by a rota-evaporation and loaded onto a column packed with silica gel. A light yellow solid (1.80 g) was obtained by column chromatography. TLC: eluent:dichloromethane/petroleum ether=1/1, R$_f$=0.4. $^1$H NMR (500 MHz, CDCl$_3$): δ 7.77 (s, 2H), 3.30 (d, 4H, J=17.3 Hz), 2.49 (s, 2H), 2.43 (s, 6H), 2.26 (s, 6H), 0.77 (s, 2H).

Synthesis of 1,4,6,9-tetramethyl-4b,5,5a,9b,10,10a-hexahydro-5,10-methanobenzo [3,4] cyclobuta[1,2-b]biphenylene-2,7-diamine and 1,4,6,9-tetramethyl-4b,5,5a9b,10,10a-hexahydro-5,10-methanobenzo[3,4]cyclobuta[1,2-b]biphenylene-2,6-diamine (v or SP-2-diamine)

In a 100 mL three neck round bottle flask, intermediate iv (300 mg, 0.77 mmol), hydrazine monohydrate (0.5 mL) and Pd/C (50 mg) were added to ethanol (30 mL) under N$_2$. The system was refluxed for 2 h and then cooled to room temperature, followed by pouring into ice-water. The precipitated solid was filtrated and re-dissolved in dichloromethane, loaded onto a column packed with silica gel. The resulting diamine (130 mg, yield: 51.2%) was obtained as a light yellow powder. TLC: ethyl acetate/petroleum ether=1/1; R$_f$=0.4; mp: 231.1° C.; $^1$HNMR (400 MHz, DMSO-d$_6$): δ 6.28 (s, 2H), 4.46 (s, 4H), 3.01 (t, 2H, J$_1$=3.8 Hz, J$_2$=3.8 Hz), 2.96 (t, 2H, J$_1$=3.8 Hz, J$_2$=3.8 Hz), 2.18 (t, 2H, J$_1$=8.82 Hz, J$_2$=8.82 Hz), 1.97 (s, 6H), 1.85 (s, 6H), 0.62 (s, 2H). $^{13}$C NMR (100 MHz, DMSO-d$_6$): δ 146.53, 146.50, 144.62, 144.52, 131.79, 131.69, 129.24, 129.21, 114.93, 114.90, 113.41, 113.38, 47.07, 47.03, 46.36, 46.35, 36.39, 36.02, 35.67, 26.58, 16.82, 16.79, 11.97, 11.95; FT-IR (wavenumber, cm$^{-1}$): 3417, 3336, 3205 (m, asymmetric N—H vibration), 2935 (s, asymmetric C—H vibration), 1618, 1600 (s, Aromatic C=C vibration), 1498, 1456,1350 (symmetric C—H rotation), 1208, 1173 (m, asymmetric C—N vibration), 850 (s, rotation of =C—H); HRMS for C$_{23}$H$_{27}$N$_2$+ [M+H]+; Calcd for 331.2169; Found: 331.2163. Anal. for C$_{23}$H$_{26}$N$_2$; Calcd. for: C, 83.59; H, 7.93; N, 8.48; Found: C, 83.61; H, 7.88; N, 8.20.

Synthesis of SP-TB-2

Intermediate v (330 mg, 1.00 mmol), dimethoxymethane (380 mg, 5.0 mmol) were cooled in an ice-bath and stirred for 15 min. Trifluoroacetic acid (2.3 mL) was added dropwise. After the addition, the solution was stirred in an ice bath for 0.5 h and then at room temperature for 3 h. A viscous solution was formed and poured into 10% ammonium hydroxide solution (100 mL). After stirring for 2 h, the solid was collected by filtration and dried in a vacuum oven at 40° C. for 2 h. Thereafter, the solid was re-dissolved in chloroform and precipitated in ethanol twice. An off-white polymer (330 mg, yield: 83.3%) was obtained. NMR spectrum is shown in FIG. 4. $^1$H NMR (700 MHz, CDCl$_3$): δ 4.42 (s, 4H), 4.23 (s, 2H), 3.87 (s, 2H), 3.14 (s, 2H), 2.25 (s, 8H), 1.92 (s, 6H), 0.75 (s, 2H); T$_{d,5\%}$=440° C.; FT-IR (wavenumber, cm$^{-1}$): 2939, 2882 (s, asymmetric C—H vibration), 1435, (s, aromatic C=C vibration), 1355 (symmetric C—H rotation), 1200, 1104 (s, asymmetric C—N vibration); S$_{BET}$=987 m$^2$ g$^{-1}$; Anal. Calcd. for: C, 86.12; H, 6.71; N, 7.17; Found: C, 87.87; H, 7.00; N, 7.66.

Film Preparation.

The ladder polymers SP-TB-1 and SP-TB-2 were dissolved in chloroform (2-3% vol/wt %). The clear solutions were filtered into a flat Petri dish by using a hydrophobic 0.45 μm PTFE filter. The solvent was evaporated for two days and light yellow transparent isotropic films (~40 to 90 μm) were obtained. The fresh membranes were soaked in methanol for 4 h and then air-dried for 3 days or dried in vacuum oven at 120° C. for 24 h, respectively. In each case, complete solvent removal was confirmed by TGA analysis.

Gas Permeation Measurements.

The gas permeability of the polymers was determined at 35° C. and 2 bar using the constant-volume/variable-pressure method by:

$$P = D \times S = 10^{10} \times \frac{V_d \times l}{p_{up} \times T \times R \times A} \times \frac{dp}{dt} \quad (2)$$

where P is the permeability (Barrer)–1 Barrer=10$^{-10}$ cm$^3$ (STP) cm cm$^{-2}$s$^{-1}$ cmHg$^{-1}$, p$_{up}$ is the upstream pressure (cmHg), dp/dt is the steady-state permeate-side pressure increase (cmHg s$^{-1}$), V$_d$ is the calibrated permeate volume (cm$^3$), l is the membrane thickness (cm), A is the effective membrane area (cm$^2$), T is the operating temperature (K), and R is the gas constant (0.278 cm$^3$ cmHg cm$^{-3}$ (STP) K$^{-1}$). The apparent diffusion coefficient D (cm$^2$ s$^{-1}$) of the polymer membrane was calculated by D=l$^2$/6θ, where l is the film thickness and θ is the time lag of the permeability measurement. The solubility coefficient S (cm$^3$ (STP) cm$^{-3}$ cmHg$^{-1}$) was obtained from the relationship S=P/D.

Results and Discussion

Synthesis, Structure and Physical Properties of the Polymers.

Figure 6A:
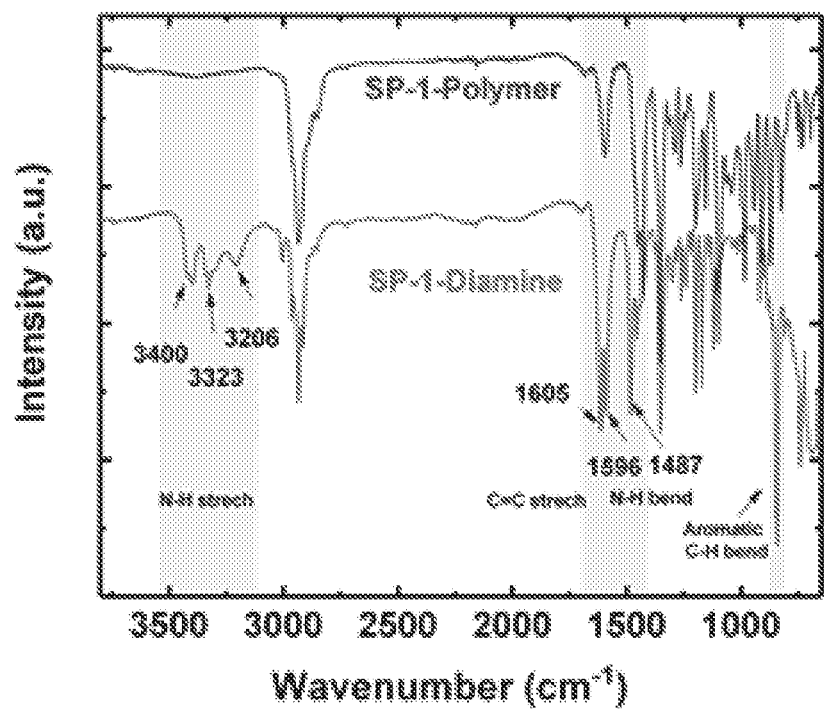
FIGS. 6A-B show the FT-IR of (A) the SP-1 diamine (i) and SP-TB-1, and (B) the SP-2 diamine (v) and SP-TB-2, according to one or more embodiments of the present disclosure.
Figure 6B:
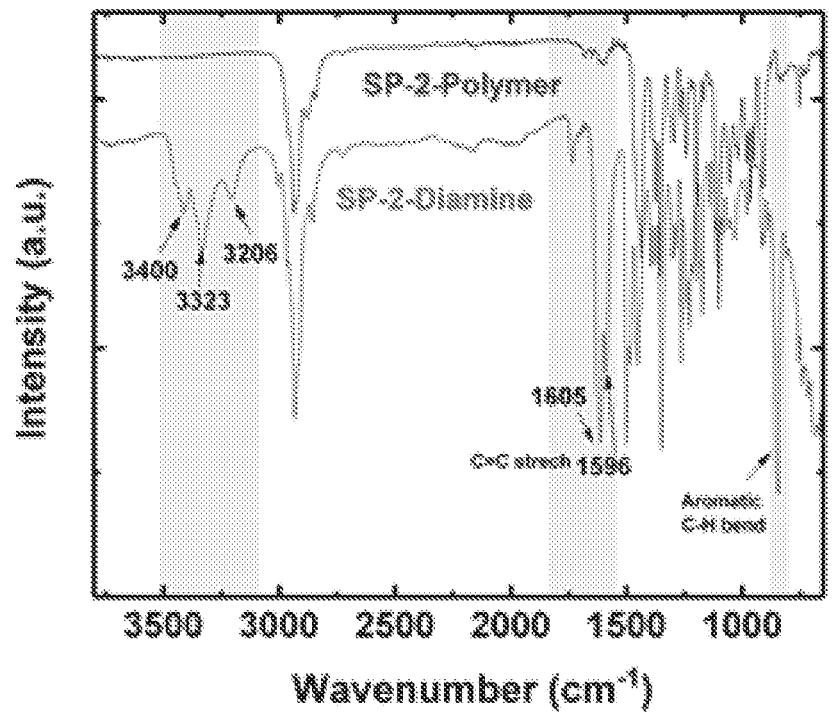

The arene-norbornene-based diamine 1 (intermediate i) was obtained by following a previously reported catalytic arene-norbornene annulation (CANAL) synthetic method. Under a catalytic amount of $Pd(OAc)_2$ and triphenylphosphine as ligand system, the aryl bromine atom was reacted with norbornadiene via ortho-C—H activation followed by reductive elimination to form the contorted fused norbornyl benzocyclobutene-based diamine (Scheme 3). The structure of the diamine (i) was identified and confirmed by its $^1$H NMR, $^{13}$CNMR, FT-IR, and HRMS as shown in FIGS. 5A-D and summarized in the above synthesis section. The resulting diamine was further reacted with dimethoxymethane to form the ladder-type Tröger's base polymer (SP-TB-1) following a recently reported procedure. The completed reaction of the diamine was confirmed by FT-IR spectra as no peaks were observed above 3000 cm$^{-1}$ (FIGS. 6A-B). The tetramethyl-substituted arene-norbornene-based diamine (intermediate v, Scheme 3) was synthesized by the following steps: tetramethyl-norbornyl benzocyclobutene (iii) was reacted with $KNO_3$ and trifluoroacetic anhydride to give the dinitro compound iv, which was further reduced to the diamine by hydrazine monohydrate using Pd/C as catalyst. The structure of this monomer was also confirmed and the corresponding Tröger's base polymer (SP-TB-2) was synthesized by the same procedure as SP-TB-1. The intermediates and polymers were fully characterized as described in the above synthesis section. The resulting ladder polymers SP-TB-1 and SP-TB-2 were readily soluble in conventional solvents such as chloroform and dichloromethane. Chloroform was chosen as casting solvent for the preparation of robust films for polymer characterizations.

TABLE 1

Physical Properties of SP-TB-1 and SP-TB-2

| Polymer | $T_{d, 5\%}$ (° C.) | $S_{BET}$ (m$^2$ g$^{-1}$) | $V_{pore}$ (cc g$^{-1}$) | $\rho$ (g cm$^{-3}$) |
|---|---|---|---|---|
| SP-TB-1 | 440 | 881 | 0.61 | 1.09 |
| SP-TB-2 | 440 | 987 | 0.66 | 1.08 |

Figure 7:
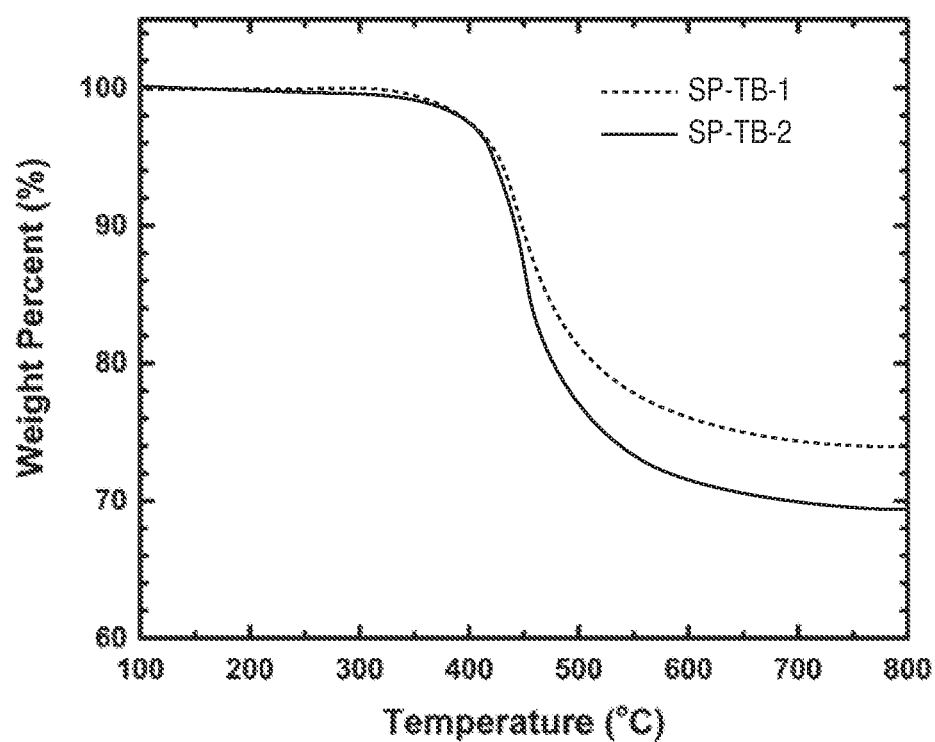
FIG. 7 shows thermal gravimetric analysis of the SP-TB-1 and SP-TB-2 films, according to one or more embodiments of the present disclosure. The samples were heated from room temperature to 800° C. at a rate of 3° C. min$^{-1}$ under N$_2$ atmosphere.
Figure 8:
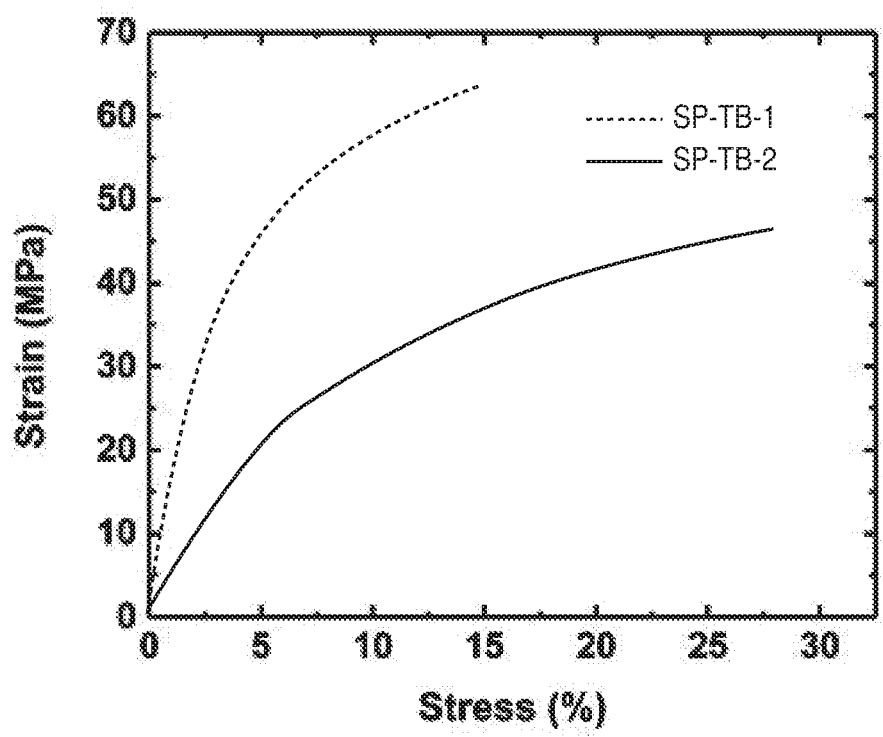
FIG. 8 shows the stress-strain curves of SP-TB-1 and SP-TB-2, according to one or more embodiments of the present disclosure.

Both SP-TB-1 and SP-TB-2 demonstrated high thermal stabilities with 5% weight loss decomposition temperature ($T_d$,5%) of ~440° C. (FIG. 7 and Table 1). Both polymers showed high charcoal remains with 76% for SP-TB-1 and 63% for SP-TB-2 at 800° C. Moreover, no glass transition temperature was detected by their DSC scans up to 350° C. Besides high thermal stability, SP-TB-1 and SP-TB-2 also demonstrated good mechanical properties with tensile strength of 63.3 and 46.3 MPa and Young's modulus of 1.63 and 0.42 GPa, respectively. The elongation at break of SP-TB-2 (28%) was much higher than SP-TB-1 (14.9%) (Table 2, FIG. 8).

TABLE 2

Mechanical Properties of SP-TB-1 and SP-TB-2

| Polymer | Young's modulus (GPa) | Tensile strength (MPa) | Elongation at break (%) |
|---|---|---|---|
| SP-TB-1 | 1.63 | 63.3 | 14.9 |
| SP-TB-2 | 0.42 | 46.3 | 28.0 |

Monomer and Polymer Geometric Optimization.

The geometric optimization of the monomers, and polymers were performed using Materials Studio (8.0) software package (Accelrys Software Inc., BIOVIA, Calif., USA). The repeat unit was optimized by Material Studio Compass forcefield using smart algorithm to ultra-fine convergence. The polymers with different repeat unit length (6 and 7) were constructed based on the growth of the optimized repeat unit. Their geometry was again optimized using Forcite modules similar to the repeat unit.

Intrinsic Microporosity of the Polymers.

The microporous texture of the ladder polymers was evaluated by $N_2$ adsorption at −196° C. Both polymers demonstrated Type I adsorption isotherms, as shown in FIG. 9A. A remarkable microporosity was demonstrated by large gas sorption uptake at low relative pressure (p/p$_0$<0.05) for both ladder polymers. SP-TB-1 showed a high BET surface area of 881 m$^2$ g$^{-1}$ and a pore volume of 0.61 cm$^3$ g$^{-1}$ (Table 1 and FIG. 9A). Because of its more constrained structure, the SP-TB-2 ladder polymer with tetramethyl substitution showed an even higher BET surface area of 987 m$^2$ g$^{-1}$ coupled with a pore volume of 0.66 cm$^3$ g$^1$ (Table 1 and FIG. 9A). This BET surface area value is among the highest of soluble intrinsically microporous polymers reported to date as compared to PIM-1 (850 m$^2$ g$^{-1}$), PIM-SBF (803 m$^2$ g$^{-1}$), KAUST-PI-1 (752 m$^2$ g$^{-1}$), PIM-PI-EA (616 m$^2$ g$^{-1}$), SBFDA-DMN (680 m$^2$ g$^{-1}$), PIM-PI-10 (699 m$^2$ g$^{-1}$) and PIM-MP-TB (743 m$^2$ g$^{-1}$), and is in the range of PIM-Trip-TB (899 m$^2$ g$^{-1}$), PIM-BTrip-TB (870 m$^2$ g$^{-1}$), PIM-EA-TB (1028 m$^2$ g$^{-1}$), PIM-TMN-Trip (1050 m$^2$ g$^{-1}$) and PIM-TMN-SBI (1015 m$^2$ g$^{-1}$). The pore size distributions of the two ladder polymers derived from $N_2$ adsorption isotherms by non-linear density functional theory (NLDFT) analysis are shown in FIG. 9B. A bimodal pore size distribution with remarkable ultra-microporosity (<7 Å) fraction was observed (FIG. 9B), which is a good indication for the potential of these PIMs to achieve significant molecular sieving properties leading to high gas-pair selectivity.

Figure 10:
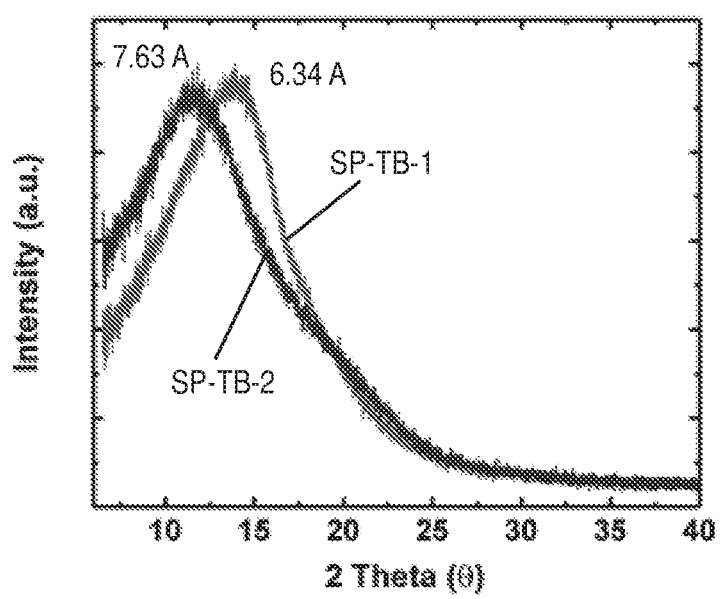
FIG. 10 shows the wide-angle X-ray scattering of SP-TB-1 and SP-TB-2 films, according to one or more embodiments of the present disclosure. The thickness of the two films were 86 and 80 μm, respectively. Both films were soaked in methanol and then dried in a vacuum oven at 120° C. for 24 h.

The amorphous structures of the two polymers were confirmed by their wide angle X-ray scattering spectra (FIG. 10). The SP-TB-1 demonstrated a halo with maximum intensity of two theta at 13.9°, corresponding to d-spacing of 6.34 Å, whereas SP-TB-2 displayed even larger d-spacing of 7.63 Å, clearly indicating a more open structure in SP-TB-2 than SP-TB-1 due to more inefficient, sterically restricted chain packing.

Gas Permeation Properties.

The gas permeation properties of the SP-TB-1 and SP-TB-2 films were determined at 2 bar and 35° C. using the constant volume/variable pressure method. Thin membranes (~39 μm) were dried under vacuum at 120° C. for 24 h. The films were treated in methanol to remove traces of casting solvent before drying. The gas permeability of the films for $H_2$, $N_2$, $O_2$, $CH_4$ and $CO_2$ as well as ideal gas-pair selectivities are summarized in Table 3.

TABLE 3

Gas Permeability and Ideal Selectivity of SP-TB-1 and SP-TB-2
(T = 35° C.; p = 2 bar) Compared to Other
Tröger's Base Ladder Polymers (PIM-TRIP-TB, PIM-EA-TB, PIM-MP-TB).

| Polymer | Permeability (barrer) | | | | | Ideal selectivity ($\alpha_{X/Y}$) | | | |
|---|---|---|---|---|---|---|---|---|---|
| | $H_2$ | $N_2$ | $O_2$ | $CH_4$ | $CO_2$ | $H_2/N_2$ | $H_2/CH_4$ | $O_2/N_2$ | $CO_2/CH_4$ |
| SP-TB-1[a] | 2760 | 97 | 463 | 121 | 1678 | 28.5 | 22.8 | 4.8 | 13.9 |
| Aged 300 d | 1163 | 39 | 204 | 53 | 749 | 29.8 | 22.0 | 5.2 | 14.1 |
| SP-TB-2[b] | 3608 | 162 | 747 | 205 | 2520 | 22.3 | 17.6 | 4.6 | 12.3 |
| Aged 300 d | 2452 | 110 | 528 | 129 | 1751 | 22.4 | 19.1 | 4.8 | 13.6 |
| PIM-TRIP-TB[c] | 8039 | 629 | 2718 | 905 | 9709 | 12.8 | 8.9 | 4.3 | 10.7 |
| Aged 100 d | 4740 | 189 | 1073 | 218 | 3951 | 25.0 | 21.7 | 5.7 | 18.1 |
| PIM-EA-TB[d] | 8114 | 580 | 2294 | 774 | 7696 | 14.0 | 10.5 | 4.0 | 9.9 |
| Aged 470 d | 4442 | 188 | 933 | 219 | 2644 | 23.6 | 20.2 | 5.0 | 12.1 |
| PIM-MP-TB[e] | 4050 | 200 | 999 | 264 | 3500 | 20.3 | 15.3 | 5.0 | 13.3 |

[a] SP-TB-1 with the thickness of 39 µm, soaked in MeOH and then dried at 120° C. under vacuum for 24 h.
[b] SP-TB-2 with thickness of 39 µm, soaked in MeOH and then dried at 120° C. under vacuum for 24 h.
[c] PIM-TRIP-TB with thickness of 132 µm, soaked in methanol and then air dried; 1 bar and 25° C.;
[d] PIM-EA-TB with thickness of 180 µm, soaked in methanol and then air dried; 1 bar and 25° C.;
[e] PIM-MP-TB with thickness of 94 µm, soaked in methanol and then air dried; 1 bar and 25° C.

Figure 11A:
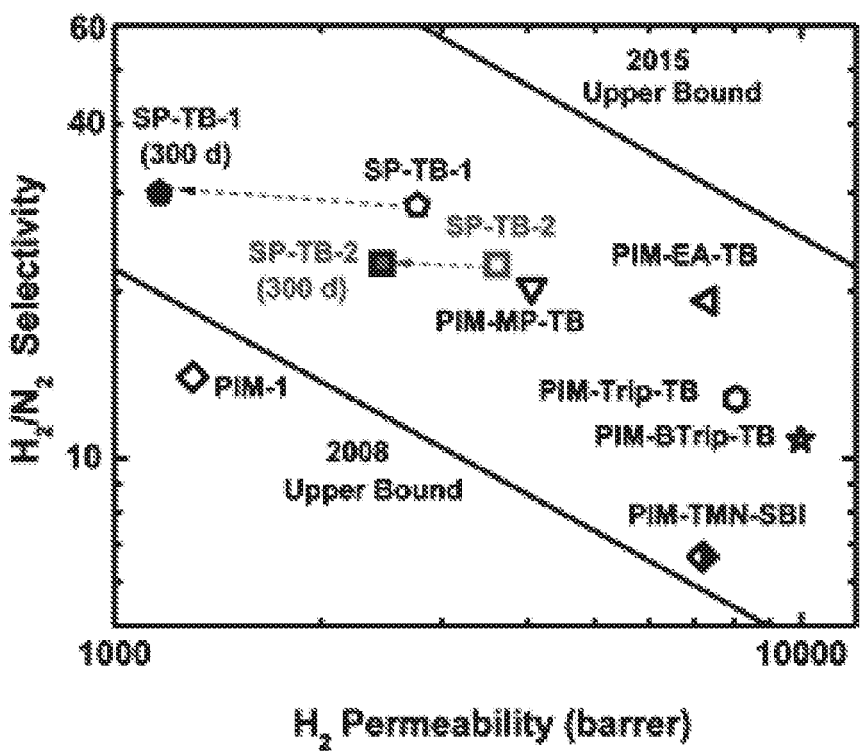
FIGS. 11A-B show (A) the H$_2$/N$_2$ and (B) the O$_2$/N$_2$ trade-off curves for SP-TB-1 and SP-TB-2, according to one or more embodiments of the present disclosure, and other previously reported ladder-type polymers.
Figure 11B:
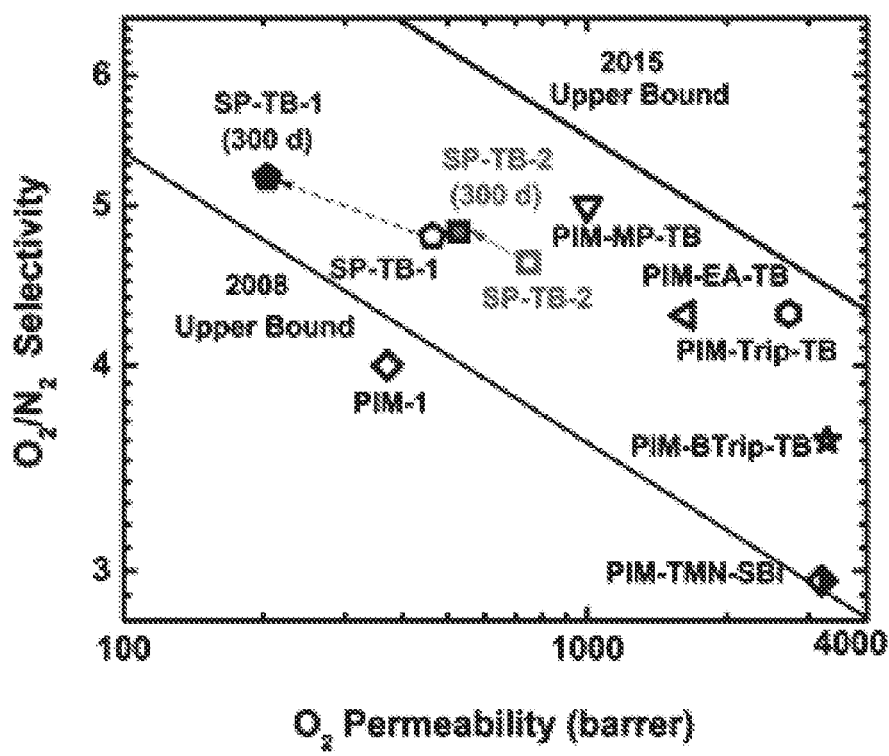

Both polymers exhibited very high gas permeability for the fresh SP-TB-1 and SP-TB-2 films as demonstrated by $H_2$ permeability of 2760 and 3608 barrer, respectively. After 300 days aging, the $H_2$ permeability dropped by ~35% for SP-TB-2 but still maintained a very high value of 2452 barrer. Different from PIM-1 or PIM-SBF, the permeability of $H_2$ was higher than $CO_2$ in both SP-TB-1 and SP-TB-2 ladder polymers. The sequence of the gas permeabilities was $PH_2>PCO_2>PO_2>PCH_4>PN_2$, which is consistent with that of other highly selective ladder PIMs membranes that have strong molecular sieving properties, such as TPIM-1, PIM-MP-TB, PIM-EA-TB, PIM-TMN-Trip-TB and aged PIM-Trip-TB. The fresh SP-TB-1 film exhibited an $O_2$ permeability of 463 barrer coupled with $O_2/N_2$ selectivity of 4.8. Because of physical aging, permeability decreased for all gases with some commensurate increase in gas-pair selectivities, especially $O_2/N_2$ (Table 3). For example, the 300 days aged SP-TB-1 film demonstrated an $O_2$ permeability of 204 barrer and $H_2/N_2$ selectivity of 5.2. The gas separation properties of SP-TB-1 and SP-TB-2 are located between the 2008 and 2015 permeability/selectivity trade-off curves for $H_2/N_2$ and $O_2/N_2$ (FIGS. 11A-B). Their performances are better than the prototype ladder PIM-1, and comparable to those of some of the best ladder-type PIMs and PIM-PIs (Table 4), such as TPIM-1, PIM-Trip-TB, PIM-BTrip-TB, PIM-MP-TB, PIM-EA-TB (Table 4). This excellent performance can be attributed to the size sieving structure induced by the IFV of the unique W-shaped CANAL building blocks (FIG. 1). In the case of $CO_2/CH_4$ separation, the selectivity of SP-TB-1 and SP-TB-2 of ~14 or less is too low to be commercially attractive, similar to other highly permeable PIMs listed in Table 3 and 4.

Monomer and Polymer Geometric Optimization.

The geometric optimization of the monomers, and polymers were performed using Materials Studio (8.0) software package (Accelrys Software Inc., (BIOVIA) CA, USA). The repeat unit was optimized by Material Studio Compass forcefield using smart algorithm to ultra-fine convergence. The polymers with different repeat unit length (6 and 7) were constructed based on the growth of the optimized repeat unit. Their geometry was again optimized using Forcite modules similar to the repeat unit.

TABLE 4

Gas Permeability and Ideal Selectivity of SP-TB-1
and SP-TB-2 in Comparison to Other Ladder PIMs.

| Polymer | Permeability (Barrer) | | | | | Ideal selectivity ($\alpha_{X/Y}$) | | | |
|---|---|---|---|---|---|---|---|---|---|
| | $H_2$ | $N_2$ | $O_2$ | $CH_4$ | $CO_2$ | $H_2/N_2$ | $H_2/CH_4$ | $O_2/N_2$ | $CO_2/CH_4$ |
| SP-TB-1[a] | 2760 | 97 | 463 | 121 | 1678 | 28.5 | 22.8 | 4.8 | 13.9 |
| Aged 300 d | 1163 | 39 | 204 | 53 | 749 | 29.8 | 22.0 | 5.2 | 14.1 |
| SP-TB-2[b,d] | 3608 | 162 | 747 | 205 | 2520 | 22.3 | 17.6 | 4.6 | 12.3 |
| Aged 300 d | 2452 | 110 | 528 | 129 | 1751 | 22.4 | 19.1 | 4.8 | 13.6 |
| PIM-1[c] | 1300 | 92 | 370 | 125 | 2300 | 14 | 10.4 | 4.0 | 18.4 |
| PIM-EA-TB[d] | 7310 | 380 | 1630 | 572 | 5100 | 19.2 | 12.8 | 4.3 | 8.92 |
| PIM-MP-TB[e] | 4050 | 200 | 999 | 264 | 3500 | 20.3 | 15.3 | 5.0 | 13.3 |
| PIM-SBF[f] | 6320 | 786 | 2640 | 1100 | 13900 | 8.1 | 5.7 | 3.4 | 12.6 |
| PIM-Trip-TB[g] | 8039 | 629 | 2718 | 905 | 9709 | 12.8 | 8.9 | 4.3 | 10.7 |
| PIM-Btrip-TB[h] | 9980 | 926 | 3290 | 1440 | 13200 | 10.8 | 6.9 | 3.6 | 9.2 |
| PIM-TMN-Trip[i] | 9590 | 1270 | 4600 | 2470 | 22500 | 7.5 | 3.9 | 3.6 | 9.1 |
| PIM-TMN-SBI[i] | 7190 | 1080 | 3200 | 2100 | 17500 | 6.7 | 3.4 | 3.0 | 8.3 |
| PIM-TMN-Trip-TB[i] | 6100 | 396 | 2030 | 710 | 6060 | 15.4 | 8.6 | 5.1 | 8.5 |

[a] SP-TB-1 with the thickness of 39 µm, soaked in MeOH and dried in 120° C. vacuum oven for 24 h.
[b] SP-TB-2 with the thickness of 39 µm, soaked in MeOH and dried in 120° C. vacuum oven for 24 h.
[c-i] Previously reported values.

TABLE 5

Diffusion Coefficients of SP-TB-1 and SP-TB-2 Films and Their $O_2/N_2$ and $CO_2/CH_4$ Diffusivity and Solubility Selectivities.

| Polymer | $D$ ($\times 10^8$ cm$^2$ s$^{-1}$) | | | | $\alpha_D(O_2/N_2)$[c] | $\alpha_S$[d] | $\alpha_D(CO_2/CH_4)$[c] | $\alpha_S$[d] |
|---|---|---|---|---|---|---|---|---|
| | $N_2$ | $O_2$ | $CH_4$ | $CO_2$ | $\alpha_D$[c] | $\alpha_S$[d] | $\alpha_D$[c] | $\alpha_S$[d] |
| SP-TB-1[a] | 22.2 | 94 | 7.0 | 34.7 | 4.22 | 1.13 | 4.95 | 2.80 |
| Aged 300 d | 11.1 | 53 | 4.1 | 20.9 | 4.78 | 1.09 | 5.09 | 2.79 |
| SP-TB-2 | 44.0 | 175 | 11.4 | 58.0 | 3.98 | 1.16 | 5.09 | 2.42 |
| Aged 300 d | 31.5 | 130 | 8.25 | 43.0 | 4.13 | 1.16 | 5.21 | 2.60 |

[a] SP-TB-1 with the thickness of 39 μm, soaked in MeOH and dried in 120° C. vacuum oven for 24 h.
[b] SP-TB-2 with the thickness of 39 μm, soaked in MeOH and dried in 120° C. vacuum oven for 24 h.
[c] Diffusivity selectivity.
[d] Solubility selectivity.

The diffusion coefficients of $N_2$, $O_2$, $CH_4$, $CO_2$ and diffusivity selectivity as well as solubility selectivities for $O_2/N_2$ and $CO_2/CH_4$ of SP-TB-1 and SP-TB-2 are shown in Table 5. The aged membranes exhibited slightly enhanced selectivity due to a small increase in diffusivity selectivity (GD) with a concurrent drop in diffusion coefficients. For example, the $O_2$ diffusion coefficient for the 300 days aged thin (39 μm) SP-TB-1 film decreased from $94 \times 10^{-8}$ to $53 \times 10^{-8}$ cm$^2$ s$^{-1}$, and the $O_2/N_2$ diffusivity selectivity increased from 4.22 to 4.78. On the other hand, physical aging had essentially no effect on the $O_2/N_2$ solubility selectivity.

Molecular dynamics (MD) simulations are shown in FIGS. 12A-F. From the side view of the optimized geometric monomer structures (FIGS. 12B and E), the protons in the tetramethyl groups are not aligned parallel to each other (highlighted in (FIGS. 12B and E as a dashed circle). Hence, the dihedral angles between the CANAL and Tröger's base moieties (FIGS. 12A and D, highlighted by upper and lower arcs) in SP-TB-1 and SP-TB-2 shifted from 75.8 to 77.3° and 164.8 to 166°, respectively. As a result, the polymer chains of SP-TB-2 tend to fold in a more twisted configuration than in SP-TB-1 (FIGS. 12C and F). The more inefficient chain packing in SP-TB-2 correlates well with the trend of experimentally measured lower density, higher BET surface area and larger average chain d-spacing.

CONCLUSIONS

Two highly intrinsically microporous ladder polymers, SP-TB-1 and SP-TB-2, were obtained by combining CANAL and Tröger's base building blocks for the first time. The two novel polymers demonstrated high thermal stability, good mechanical strength, and high BET surface area. Isotropic films based on these polymers showed excellent gas separation properties, with performance located between the 2008 and 2015 permeability/selectivity upper bound lines for $H_2/N_2$ and $O_2/N_2$. After aging, the $H_2$ permeability for SP-TB-1 reached 1163 barrer with an $H_2/N_2$ selectivity of 29.8 (FIGS. 11A-B). Both SP-TB-1 and SP-TB-2 demonstrated very high permeability for $H_2$, $O_2$, and $CO_2$. The $H_2$ permeability can be as high as ~3600 Barrer (FIG. 11A). Moreover, these results show good selectivity for $H_2/N_2$, $H_2/CH_4$, and $O_2/N_2$. The $H_2/N_2$ and $O_2/N_2$ performance for SP-TB-1 and SP-TB-2 treated at different conditions and aged for different times (data not shown).

The strong size sieving properties maybe due to the high rigidity and internal free volume of the W-shaped CANAL structure. The SP-TB-2 polymer exhibited a more open internal structure than SP-TB-1, as indicated by its higher surface area, lower density, larger average chain d-spacing, higher gas permeability and lower gas pair selectivity.

Other embodiments of the present disclosure are possible. Although the description above contains much specificity, these should not be construed as limiting the scope of the disclosure, but as merely providing illustrations of some of the presently preferred embodiments of this disclosure. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form various embodiments. Thus, it is intended that the scope of at least some of the present disclosure should not be limited by the particular disclosed embodiments described above.

The scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

The foregoing description of various preferred embodiments of the disclosure have been presented for purposes of illustration and description. It is not intended to be exhaustive or to limit the disclosure to the precise embodiments, and obviously many modifications and variations are possible in light of the above teaching. The example embodiments, as described above, were chosen and described in order to best explain the principles of the disclosure and its practical application to thereby enable others skilled in the art to best utilize the disclosure in various embodiments and with various modifications as are suited to the particular use contemplated. It is intended that the scope of the disclosure be defined by the claims appended hereto Various examples have been described. These and other examples are within the scope of the following claims.

What is claimed is:

1. A composition comprising an intrinsically microporous ladder-type Tröger's base polymer comprising a repeat unit represented by formula (I):

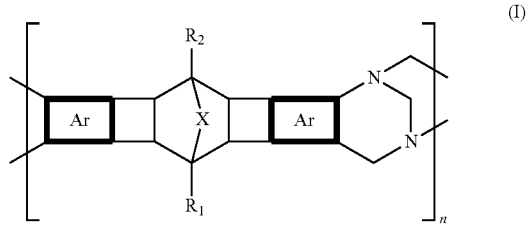

wherein each Ar is independently selected from an unsubstituted or substituted aryl group; X is a carbon or heteroatom bridging moiety selected from —[O]—, —[S]—, —[B(O)R$^a$]—, —[NR$^a$]—, —[P(O)R$^a$]—, —[(PO)(O)R$^a$]—, —[CO]—, —[—CR$^a$R$^b$]—, —[C(O)R$^a$(O)R$^b$]—, or —[Si(O)R$^a$(O)R$^b$]—, and R$^a$ and R$^b$ are independently selected from the group consisting of hydrogen, alkyl groups, aryl groups, and heterocyclic groups; $R_1$ and $R_2$ are independently selected from the group consisting of hydrogen, linear unsubstituted and substituted alkyl groups, branched unsubstituted and substituted alkyl groups, unsubstituted and substituted alkoxy groups, unsubstituted and substituted aryl groups, heterocyclic groups, halogen groups, —CHO, groups having an —O— moiety, groups having an —O(CO)— moiety, groups having an —O(CO)O— moiety, groups having an —O(CO)N< moiety, groups having a —S— moiety, groups having a —B< moiety, —NO$_2$, groups having a —N< moiety, groups having a —P< moiety, groups having a —(PO)< moiety, groups having a —(CO)— moiety, groups having a —(CO)O— moiety, groups having a —(CO)N< moiety and groups having a —Si≡ moiety; and n is an integer greater than 1.

2. The composition of claim 1, wherein the intrinsically microporous ladder-type Tröger's base polymer has a BET surface area greater than about 600 m$^2$ g$^{-1}$.

3. The composition of claim 1, wherein X is a carbon, $R_1$ and $R_2$ are hydrogen, and each Ar is independently selected from the group consisting of:

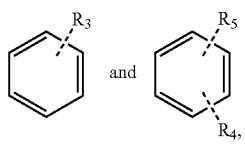

wherein $R_3$, $R_4$, and $R_5$ are each independently selected from the group consisting of linear unsubstituted or substituted alkyl groups, branched unsubstituted or substituted alkyl groups, unsubstituted or substituted alkoxy groups, unsubstituted or substituted unsaturated aliphatic groups, unsubstituted or substituted cycloalkyl groups, unsubstituted or substituted aryl groups, unsubstituted or substituted heterocyclic groups, —CHO, groups having a —O— moiety, groups having a —O(CO)— moiety, groups having a —O(CO)O— moiety), groups having a —O(CO)N< moiety, groups having a —S— moiety, groups having a —B< moiety, —NO$_2$, groups having a —N< moiety, groups having a —P< moiety, groups having a —PO< moiety, groups having a —(CO)— moiety, groups having a —(CO)O— moiety, groups having a —(CO)N< moiety, and groups having a —Si≡ moiety.

4. The composition of claim 1, wherein n is greater than 5.

5. The composition of claim 1, wherein the repeat unit has the following structure:

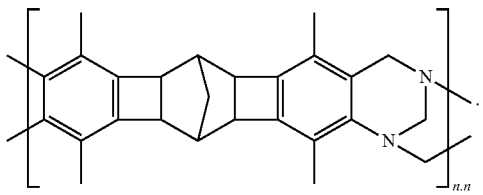

6. The composition of claim 1, wherein the repeat unit has the following structure:

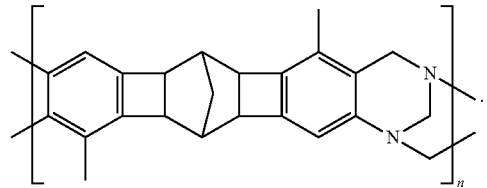

7. The composition of claim 1, wherein the composition is configured as a flat sheet membrane, a rolled flat sheet membrane, a supported membrane, a cylinder, a tube, a capillary, a hollow fiber, or a powder.

8. The composition of claim 7, wherein the composition has a thickness of about 1 to 30 μm.

9. The composition of claim 1, wherein the intrinsically microporous ladder-type Tröger's base polymer has a bimodal pore size distribution comprising ultramicropores.

10. A method of synthesizing an intrinsically microporous ladder-type Tröger's base polymer comprising:
(a) forming a ladder-type diamine monomer by catalytic arene-norbornene annulation (CANAL) polymerization of a halogenated arylamine and norbornadiene or a derivative thereof, wherein the molar ratio of the halogenated arylamine to norbornadiene or the derivative thereof is 2:1, or
(a1) forming a first intermediate ladder-type compound by CANAL polymerization of a halogenated arene and norbornadiene or a derivative thereof, wherein the ratio of the halogenated arene to norbornadiene or the derivative thereof is 2:1; and
(a2) nitrating the first intermediate ladder-type compound to form an intermediate ladder-type dinitro compound; and
(a3) reducing the two nitro groups of the intermediate ladder-type dinitro compound to form a ladder-type diamine monomer; and
(b) reacting at least two of the ladder-type diamine monomers to form the intrinsically microporous ladder-type Tröger's base polymer comprising a repeat unit represented by formula (I):

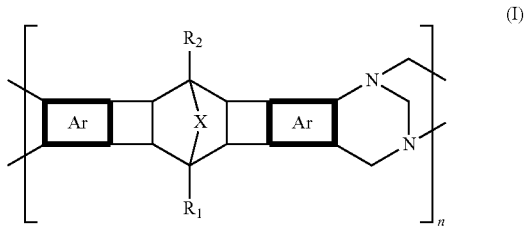

wherein each Ar is independently selected from an unsubstituted or substituted aryl group; X is a carbon or heteroatom bridging moiety selected from —[O]—, —[S]—, —[B(O)R$^a$]—, —[NR$^a$]—, —[P(O)R$^a$]—, —[(PO)(O)R$^a$]—, —[CO]—, —[—CR$^a$R$^b$]—, —[C(O)R$^a$(O)R$^b$]—, or —[Si(O)R$^a$(O)R$^b$]—, and R$^a$ and R$^b$ are independently selected from the group consisting of hydrogen, alkyl groups, aryl groups, and heterocyclic groups; $R_1$ and $R_2$ are independently selected from the group consisting of hydrogen, linear unsubstituted and substituted alkyl groups, branched unsubstituted and substituted alkyl groups, unsubstituted and substituted alkoxy groups, unsubstituted and substituted aryl groups, heterocyclic groups, halogen groups, —CHO, groups having an —O— moiety, groups having an —O(CO)— moiety, groups having an —O(CO)O— moiety, groups having an —O(CO)N< moiety, groups having a —S— moiety, groups having a —B< moiety, —NO$_2$, groups having a —N< moiety, groups having a —P< moiety, groups having a —(PO)< moiety, groups having a —(CO)— moiety, groups having a —(CO)O— moiety, groups having a —(CO)N< moiety and groups having a —Si≡ moiety; and n is an integer greater than 1.

11. The method of claim 10, comprising performing step (a), wherein the halogenated arylamine has the following structure:

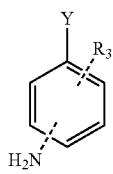

wherein Y is a chloro, bromo, or iodo group; and R$_3$ is selected from the group consisting of linear unsubstituted or substituted alkyl groups, branched unsubstituted or substituted alkyl groups, unsubstituted or substituted unsaturated aliphatic groups, unsubstituted or substituted cycloalkyl groups, unsubstituted or substituted aryl groups, unsubstituted or substituted heterocyclic groups, unsubstituted or substituted alkoxy groups, —CHO, groups having a —O— moiety, groups having a —O(CO)— moiety, groups having a —O(CO)O— moiety), groups having a —O(CO)N< moiety, groups having a —S— moiety, groups having a —B< moiety, —NO$_2$, groups having a —N< moiety, groups having a —P< moiety, groups having a —PO< moiety, groups having a —(CO)— moiety, groups having a —(CO)O— moiety, groups having a —(CO)N< moiety, and groups having a —Si≡ moiety.

12. The method of claim 10, comprising performing steps (a1)-(a3), wherein the halogenated arene has the following structure:

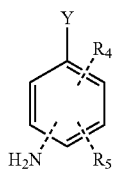

wherein Y is a chloro, bromo, or iodo group; and R$_4$ and R$_5$ are independently selected from the group consisting of linear unsubstituted or substituted alkyl groups, branched unsubstituted or substituted alkyl groups, unsubstituted or substituted unsaturated aliphatic groups, unsubstituted or substituted cycloalkyl groups, unsubstituted or substituted aryl groups, unsubstituted or substituted heterocyclic groups, linear unsubstituted or substituted alkoxy groups, branched unsubstituted or substituted alkoxy groups, —CHO, groups having a —O— moiety, groups having a —O(CO)— moiety, groups having a —O(CO)O— moiety), groups having a —O(CO)N< moiety, groups having a —S— moiety, groups having a —B< moiety, —NO$_2$, groups having a —N< moiety, groups having a —P< moiety, groups having a —PO< moiety, groups having a —(CO)— moiety, groups having a —(CO)O— moiety, groups having a —(CO)N< moiety, and groups having a —Si≡ moiety.

13. The method of claim 12, wherein nitrating includes contacting the first intermediate compound with an inorganic nitrate and one of a carboxylic acid or carboxylic acid anhydride.

14. The method of claim 12, wherein reducing includes catalytic hydrogenation.

15. The method of claim 14, wherein catalytic hydrogenation comprises refluxing the intermediate dinitro compound in the presence of hydrazine monohydrate and palladium on carbon.

16. The method of claim 10, wherein step (b) comprises reacting the ladder-type diamine monomers with a formaldehyde source and a Lewis acid catalyst.

17. A method of separating a chemical species in a fluid composition comprising:
(a) contacting a membrane comprising an intrinsically microporous ladder-type Tröger's base polymer with a fluid composition comprising at least two chemical species; and
(b) separating a first chemical species from the fluid composition;
wherein the intrinsically microporous ladder-type Tröger's base polymer comprises a repeat unit represented by formula (I):

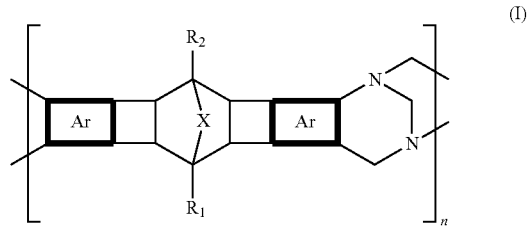

wherein each Ar is independently selected from an unsubstituted or substituted aryl group; X is a carbon or heteroatom bridging moiety selected from —[O]—, —[S]—, —[B(O)R$^a$]—, —[NR$^a$]—, —[P(O)R$^a$]—, —[(PO)(O)R$^a$]—, —[CO]—, —[—CR$^a$R$^b$]—, —[C(O)R$^a$(O)R$^b$]—, or —[Si(O)R$^a$(O)R$^b$]—, and R$^a$ and R$^b$ are independently selected from the group consisting of hydrogen, alkyl groups, aryl groups, and heterocyclic groups; R$_1$ and R$_2$ are independently selected from the group consisting of hydrogen, linear unsubstituted and substituted alkyl groups, branched unsubstituted and substituted alkyl groups, unsubstituted and substituted alkoxy groups, unsubstituted and substituted aryl groups, heterocyclic groups, halogen groups, —CHO, groups having an —O— moiety, groups having an —O(CO)— moiety, groups having an —O(CO)O— moiety, groups having an —O(CO)N< moiety, groups having a —S— moiety, groups having a —B< moiety, —NO$_2$, groups having a —N< moiety, groups having a —P< moiety, groups having a —(PO)< moiety, groups having a —(CO)— moiety, groups having a —(CO)O— moiety, groups having a —(CO)N< moiety and groups having a —Si≡ moiety; and n is an integer greater than 1.

18. The method of claim 17, wherein the fluid composition is selected from the group consisting of air, natural gas, flue gas, ammonia synthesis purge streams, hydrocarbon processing gas, steam reforming gas, gasification process gas, off-gases from refinery or petrochemical plants, and a combination thereof.

19. The method of claim 17, wherein the fluid composition comprises a gaseous chemical species selected from the group consisting of $H_2$, $O_2$, $N_2$, Ar and $CO_2$.

20. The method of claim 17, wherein the membrane is permeable to one or more of $H_2$, $O_2$, $N_2$, Ar and $CO_2$.

\* \* \* \* \*